(12) United States Patent
Shelton, IV et al.

(10) Patent No.: US 7,464,849 B2
(45) Date of Patent: Dec. 16, 2008

(54) ELECTRO-MECHANICAL SURGICAL INSTRUMENT WITH CLOSURE SYSTEM AND ANVIL ALIGNMENT COMPONENTS

(75) Inventors: Frederick E. Shelton, IV, New Vienna, OH (US); Stephen J. Balek, Miamisburg, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/344,021

(22) Filed: Jan. 31, 2006

(65) Prior Publication Data

US 2007/0175961 A1     Aug. 2, 2007

(51) Int. Cl.
*A61B 17/39* (2006.01)

(52) U.S. Cl. .................. 227/178.1; 227/19; 227/175.1; 227/179.1; 227/180.1

(58) Field of Classification Search .............. 227/178.1, 227/179.1, 19, 181.1
See application file for complete search history.

(56) References Cited

U.S. PATENT DOCUMENTS

| | | | |
|---|---|---|---|
| 2,037,727 | A | 4/1936 | Chapelle |
| 3,269,630 | A | 8/1966 | Fleischer |
| 3,551,987 | A | 1/1971 | Wilkinson |
| 3,643,851 | A | 2/1972 | Green et al. |
| 3,662,939 | A | 5/1972 | Bryan |
| 3,717,294 | A | 2/1973 | Green |
| 3,734,207 | A | 5/1973 | Fishbein |
| 3,819,100 | A | 6/1974 | Noiles et al. |
| 3,892,228 | A | 7/1975 | Mitsui |
| 3,894,174 | A | 7/1975 | Cartun |
| 3,940,844 | A | 3/1976 | Colby et al. |
| 4,213,562 | A | 7/1980 | Garrett et al. |
| 4,331,277 | A | 5/1982 | Green |
| 4,349,028 | A | 9/1982 | Green |
| 4,383,634 | A | 5/1983 | Green |
| 4,402,445 | A | 9/1983 | Green |

(Continued)

FOREIGN PATENT DOCUMENTS

CA         2458946 A1      3/2003

(Continued)

OTHER PUBLICATIONS

European Search Report, Application No. 07250393.1, dated Aug. 9, 2007 (8 pages).

(Continued)

*Primary Examiner*—Brian D Nash

(57) ABSTRACT

A surgical instrument. Various embodiments relate to a surgical cutting and fastening instrument that has an end effector with an anvil that can pivot between open and closed positions relative to an elongate channel that can support a staple cartridge therein. The anvil may be opened and closed by a drive system. Various embodiments employ a powered drive system for opening and closing the anvil and powering a knife and staple drive assembly used to cut tissue and deploy the staples in the cartridge. Other embodiments employ a mechanical system to open and close the anvil and employ a powered system to power the knife and staple drive assembly. In various embodiments, the drive assembly serves to axially and laterally align anvil relative to the elongate channel. The anvil is constructed to move in a substantially parallel path relative to the elongate channel during closing.

27 Claims, 24 Drawing Sheets

U.S. PATENT DOCUMENTS

| | | |
|---|---|---|
| 4,415,112 A | 11/1983 | Green |
| 4,475,679 A | 10/1984 | Fleury, Jr. |
| 4,500,024 A | 2/1985 | DiGiovanni et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,605,001 A | 8/1986 | Rothfuss et al. |
| 4,606,343 A | 8/1986 | Conta et al. |
| 4,608,981 A | 9/1986 | Rothfuss et al. |
| 4,610,383 A | 9/1986 | Rothfuss et al. |
| 4,629,107 A | 12/1986 | Fedotov et al. |
| 4,671,445 A | 6/1987 | Barker et al. |
| 4,709,120 A | 11/1987 | Pearson |
| 4,715,520 A | 12/1987 | Roehr, Jr. et al. |
| 4,728,020 A | 3/1988 | Green et al. |
| 4,728,876 A | 3/1988 | Mongeon et al. |
| 4,729,260 A | 3/1988 | Dudden |
| 4,754,909 A | 7/1988 | Barker et al. |
| 4,767,044 A | 8/1988 | Green |
| 4,790,225 A | 12/1988 | Moody et al. |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 5,027,834 A | 7/1991 | Pruitt |
| 5,031,814 A | 7/1991 | Tompkins et al. |
| 5,040,715 A | 8/1991 | Green et al. |
| 5,061,269 A | 10/1991 | Muller |
| 5,065,929 A | 11/1991 | Schulze et al. |
| 5,080,556 A | 1/1992 | Carreno |
| 5,084,057 A | 1/1992 | Green et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,156,315 A | 10/1992 | Green et al. |
| 5,171,247 A | 12/1992 | Hughett et al. |
| 5,171,249 A | 12/1992 | Stefanchik et al. |
| 5,200,280 A | 4/1993 | Karasa |
| 5,207,697 A | 5/1993 | Carusillo et al. |
| 5,211,649 A | 5/1993 | Kohler et al. |
| 5,240,163 A | 8/1993 | Stein et al. |
| 5,246,156 A | 9/1993 | Rothfuss et al. |
| 5,253,793 A | 10/1993 | Green et al. |
| RE34,519 E | 1/1994 | Fox et al. |
| 5,275,323 A | 1/1994 | Schulze et al. |
| 5,307,976 A | 5/1994 | Olson et al. |
| 5,309,927 A | 5/1994 | Welch |
| 5,318,221 A | 6/1994 | Green et al. |
| 5,330,502 A | 7/1994 | Hassler et al. |
| 5,332,142 A | 7/1994 | Robinson et al. |
| 5,339,799 A | 8/1994 | Kami et al. |
| 5,350,400 A | 9/1994 | Esposito et al. |
| 5,379,933 A | 1/1995 | Green et al. |
| 5,383,880 A | 1/1995 | Hooven |
| 5,383,881 A | 1/1995 | Green et al. |
| 5,389,098 A | 2/1995 | Tsuruta et al. |
| 5,391,180 A | 2/1995 | Tovey et al. |
| 5,395,033 A | 3/1995 | Byrne et al. |
| 5,395,312 A | 3/1995 | Desai |
| 5,397,046 A | 3/1995 | Savage et al. |
| 5,403,312 A | 4/1995 | Yates et al. |
| 5,405,344 A | 4/1995 | Williamson et al. |
| 5,409,498 A | 4/1995 | Braddock et al. |
| 5,413,267 A | 5/1995 | Solyntjes et al. |
| 5,413,268 A | 5/1995 | Green et al. |
| 5,415,335 A | 5/1995 | Knodell, Jr. |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,445,304 A | 8/1995 | Plyley et al. |
| 5,447,513 A | 9/1995 | Davison et al. |
| 5,449,365 A | 9/1995 | Green et al. |
| 5,456,401 A | 10/1995 | Green et al. |
| 5,458,579 A | 10/1995 | Chodorow et al. |
| 5,462,215 A | 10/1995 | Viola et al. |
| 5,465,895 A | 11/1995 | Knodel et al. |
| 5,465,896 A | 11/1995 | Allen et al. |
| 5,467,911 A | 11/1995 | Tsuruta et al. |
| 5,470,006 A | 11/1995 | Rodak |
| 5,472,132 A | 12/1995 | Savage et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,518,163 A | 5/1996 | Hooven |
| 5,518,164 A | 5/1996 | Hooven |
| 5,522,817 A | 6/1996 | Sander et al. |
| 5,527,320 A | 6/1996 | Carruthers et al. |
| 5,529,235 A | 6/1996 | Boiarski et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,547,117 A | 8/1996 | Hamblin et al. |
| 5,549,628 A | 8/1996 | Cooper et al. |
| 5,553,675 A | 9/1996 | Pitzen et al. |
| 5,554,169 A | 9/1996 | Green et al. |
| 5,558,665 A | 9/1996 | Kieturakis |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,574,431 A | 11/1996 | McKeown et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |

| | | | | | |
|---|---|---|---|---|---|
| 5,597,107 A | 1/1997 | Knodel et al. | 5,799,857 A | 9/1998 | Robertson et al. |
| 5,601,224 A | 2/1997 | Bishop et al. | 5,807,393 A | 9/1998 | Williamson, IV et al. |
| 5,603,443 A | 2/1997 | Clark et al. | 5,810,811 A | 9/1998 | Yates et al. |
| 5,605,272 A | 2/1997 | Witt et al. | 5,817,093 A | 10/1998 | Williamson, IV et al. |
| 5,605,273 A | 2/1997 | Hamblin et al. | 5,817,109 A | 10/1998 | McGarry et al. |
| 5,607,094 A | 3/1997 | Clark et al. | 5,817,119 A | 10/1998 | Klieman et al. |
| 5,607,095 A | 3/1997 | Smith et al. | 5,820,009 A | 10/1998 | Melling et al. |
| 5,609,285 A | 3/1997 | Grant et al. | 5,823,066 A | 10/1998 | Huitema et al. |
| 5,626,587 A | 5/1997 | Bishop et al. | 5,826,776 A | 10/1998 | Schulze et al. |
| 5,628,446 A | 5/1997 | Geiste et al. | 5,829,662 A | 11/1998 | Allen et al. |
| 5,630,539 A | 5/1997 | Plyley et al. | 5,833,690 A | 11/1998 | Yates et al. |
| 5,630,540 A | 5/1997 | Blewett | 5,836,503 A | 11/1998 | Ehrenfels et al. |
| 5,632,432 A | 5/1997 | Schulze et al. | 5,836,960 A | 11/1998 | Kolesa et al. |
| 5,634,584 A | 6/1997 | Okorocha et al. | 5,839,639 A | 11/1998 | Sauer et al. |
| 5,636,779 A | 6/1997 | Palmer | 5,843,132 A | 12/1998 | Ilvento |
| 5,636,780 A | 6/1997 | Green et al. | 5,855,311 A | 1/1999 | Hamblin et al. |
| 5,639,008 A | 6/1997 | Gallagher et al. | 5,865,361 A | 2/1999 | Milliman et al. |
| 5,643,291 A | 7/1997 | Pier et al. | 5,871,135 A | 2/1999 | Williamson IV et al. |
| 5,645,209 A | 7/1997 | Green et al. | 5,873,885 A | 2/1999 | Weidenbenner |
| 5,647,526 A | 7/1997 | Green et al. | 5,878,937 A | 3/1999 | Green et al. |
| 5,651,491 A | 7/1997 | Heaton et al. | 5,878,938 A | 3/1999 | Bittner et al. |
| 5,653,374 A | 8/1997 | Young et al. | 5,893,506 A | 4/1999 | Powell |
| 5,657,921 A | 8/1997 | Young et al. | 5,894,979 A | 4/1999 | Powell |
| 5,658,300 A | 8/1997 | Bito et al. | 5,901,895 A | 5/1999 | Heaton et al. |
| 5,662,258 A | 9/1997 | Knodel et al. | 5,911,353 A | 6/1999 | Bolanos et al. |
| 5,662,662 A | 9/1997 | Bishop et al. | 5,915,616 A | 6/1999 | Viola et al. |
| 5,667,517 A | 9/1997 | Hooven | 5,918,791 A | 7/1999 | Sorrentino et al. |
| 5,669,544 A | 9/1997 | Schulze et al. | 5,931,853 A | 8/1999 | McEwen et al. |
| 5,673,840 A | 10/1997 | Schulze et al. | 5,938,667 A | 8/1999 | Peyser et al. |
| 5,673,841 A | 10/1997 | Schulze et al. | 5,941,442 A | 8/1999 | Geiste et al. |
| 5,673,842 A | 10/1997 | Bittner et al. | 5,951,552 A | 9/1999 | Long et al. |
| 5,678,748 A | 10/1997 | Plyley et al. | 5,951,574 A | 9/1999 | Stefanchik et al. |
| 5,680,981 A | 10/1997 | Mililli et al. | 5,954,259 A | 9/1999 | Viola et al. |
| 5,680,982 A | 10/1997 | Schulze et al. | 5,988,479 A | 11/1999 | Palmer |
| 5,680,983 A | 10/1997 | Plyley et al. | 6,010,054 A | 1/2000 | Johnson et al. |
| 5,685,474 A | 11/1997 | Seeber | 6,017,356 A | 1/2000 | Frederick et al. |
| 5,688,270 A | 11/1997 | Yates et al. | 6,022,352 A | 2/2000 | Vandewalle |
| 5,690,269 A | 11/1997 | Bolanos et al. | 6,024,741 A | 2/2000 | Williamson, IV et al. |
| 5,692,668 A | 12/1997 | Schulze et al. | 6,024,748 A | 2/2000 | Manzo et al. |
| 5,693,042 A | 12/1997 | Boiarski et al. | 6,032,849 A | 3/2000 | Mastri et al. |
| 5,697,543 A | 12/1997 | Burdorff | 6,079,606 A | 6/2000 | Milliman et al. |
| 5,700,270 A | 12/1997 | Peyser et al. | 6,082,577 A | 7/2000 | Coates et al. |
| 5,702,408 A | 12/1997 | Wales et al. | 6,083,234 A | 7/2000 | Nicholas et al. |
| 5,704,534 A | 1/1998 | Huitema et al. | 6,102,271 A | 8/2000 | Longo et al. |
| 5,706,997 A | 1/1998 | Green et al. | 6,109,500 A | 8/2000 | Alli et al. |
| 5,706,998 A | 1/1998 | Plyley et al. | H1904 H | 10/2000 | Yates et al. |
| 5,709,334 A | 1/1998 | Sorrentino et al. | 6,126,670 A | 10/2000 | Walker et al. |
| 5,709,680 A | 1/1998 | Yates et al. | 6,131,789 A | 10/2000 | Schulze et al. |
| 5,711,472 A | 1/1998 | Bryan | 6,155,473 A | 12/2000 | Tompkins et al. |
| 5,713,505 A | 2/1998 | Huitema | 6,156,056 A | 12/2000 | Kearns et al. |
| 5,715,988 A | 2/1998 | Palmer | 6,162,208 A | 12/2000 | Hipps |
| 5,718,359 A | 2/1998 | Palmer et al. | 6,202,914 B1 | 3/2001 | Geiste et al. |
| 5,732,871 A | 3/1998 | Clark et al. | 6,223,835 B1 | 5/2001 | Habedank et al. |
| 5,735,445 A | 4/1998 | Vidal et al. | 6,241,139 B1 | 6/2001 | Milliman et al. |
| 5,743,456 A | 4/1998 | Jones et al. | 6,250,532 B1 | 6/2001 | Green et al. |
| 5,747,953 A | 5/1998 | Philipp | 6,264,086 B1 | 7/2001 | McGuckin, Jr. |
| 5,749,893 A | 5/1998 | Vidal et al. | 6,264,087 B1 | 7/2001 | Whitman |
| 5,752,644 A | 5/1998 | Bolanos et al. | 6,273,897 B1 | 8/2001 | Dalessandro et al. |
| 5,758,814 A | 6/1998 | Gallagher et al. | 6,309,403 B1 | 10/2001 | Minor et al. |
| 5,762,255 A | 6/1998 | Chrisman et al. | 6,315,184 B1 | 11/2001 | Whitman |
| 5,762,256 A | 6/1998 | Mastri et al. | 6,320,123 B1 | 11/2001 | Reimers |
| 5,779,130 A | 7/1998 | Alesi et al. | 6,325,810 B1 | 12/2001 | Hamilton et al. |
| 5,782,396 A | 7/1998 | Mastri et al. | 6,330,965 B1 | 12/2001 | Milliman et al. |
| 5,782,397 A | 7/1998 | Koukline | 6,358,224 B1 | 3/2002 | Tims et al. |
| 5,782,749 A | 7/1998 | Riza | 6,416,486 B1 | 7/2002 | Wampler |
| 5,782,859 A | 7/1998 | Nicholas et al. | 6,443,973 B1 | 9/2002 | Whitman |
| 5,785,232 A | 7/1998 | Vidal et al. | 6,488,197 B1 | 12/2002 | Whitman |
| 5,792,165 A | 8/1998 | Klieman et al. | 6,491,201 B1 | 12/2002 | Whitman |
| 5,794,834 A | 8/1998 | Hamblin et al. | 6,503,257 B2 | 1/2003 | Grant et al. |
| 5,796,188 A | 8/1998 | Bays | 6,505,768 B2 | 1/2003 | Whitman |
| 5,797,536 A | 8/1998 | Smith et al. | 6,511,468 B1 | 1/2003 | Cragg et al. |
| 5,797,537 A | 8/1998 | Oberlin et al. | 6,522,101 B2 | 2/2003 | Malackowski |
| 5,797,538 A | 8/1998 | Heaton et al. | 6,550,546 B2 | 4/2003 | Thurler et al. |

| | | |
|---|---|---|
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,705,503 B1 | 3/2004 | Pedicini et al. |
| 6,716,232 B1 | 4/2004 | Vidal et al. |
| 6,716,233 B1 | 4/2004 | Whitman |
| 6,752,816 B2 | 6/2004 | Culp et al. |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,817,509 B2 | 11/2004 | Geiste et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,036,680 B1 | 5/2006 | Flannery |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,066,944 B2 | 6/2006 | Laufer et al. |
| 7,077,856 B2 | 7/2006 | Whitman |
| 7,083,075 B2 | 8/2006 | Swayze et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,098,794 B2 | 8/2006 | Lindsay et al. |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,225,964 B2 | 6/2007 | Mastri et al. |
| 7,246,734 B2 | 7/2007 | Shelton, IV |
| 7,258,262 B2 | 8/2007 | Mastri et al. |
| 2002/0117534 A1 | 8/2002 | Green et al. |
| 2002/0165541 A1 | 11/2002 | Whitman |
| 2003/0105478 A1 | 6/2003 | Whitman et al. |
| 2003/0130677 A1 | 7/2003 | Whitman et al. |
| 2003/0216778 A1 | 11/2003 | Weadock |
| 2004/0028502 A1 | 2/2004 | Cummins |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0111081 A1 | 6/2004 | Whitman |
| 2004/0116952 A1 | 6/2004 | Sakurai et al. |
| 2004/0122471 A1 | 6/2004 | Toby et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0230214 A1 | 11/2004 | Donofrio et al. |
| 2004/0232199 A1 | 11/2004 | Shelton, IV et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0033357 A1 | 2/2005 | Braun |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0103819 A1 | 5/2005 | Racenet et al. |
| 2005/0107824 A1 | 5/2005 | Hilstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0145671 A1 | 7/2005 | Viola |
| 2005/0165415 A1 | 7/2005 | Wales |
| 2005/0171522 A1 | 8/2005 | Christopherson |
| 2005/0173490 A1 | 8/2005 | Shelton, IV |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0047303 A1 | 3/2006 | Ortiz et al. |
| 2006/0047308 A1 | 3/2006 | Ortiz et al. |
| 2006/0049229 A1 | 3/2006 | Milliman et al. |
| 2006/0060630 A1 | 3/2006 | Shelton, IV et al. |
| 2006/0087442 A1 | 4/2006 | Smith et al. |
| 2006/0097026 A1 | 5/2006 | Shelton, IV |
| 2006/0100643 A1 | 5/2006 | Laufer et al. |
| 2006/0108393 A1 | 5/2006 | Heinrich et al. |
| 2006/0122636 A1 | 6/2006 | Bailley et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2006/0190029 A1 | 8/2006 | Wales |
| 2006/0190031 A1 | 8/2006 | Wales et al. |

| | | | | | | |
|---|---|---|---|---|---|---|
| 2006/0226196 A1 | 10/2006 | Huell et al. | EP | 0600182 | A2 | 6/1994 |
| 2006/0229665 A1 | 10/2006 | Wales et al. | EP | 0630612 | A1 | 12/1994 |
| 2006/0278681 A1 | 12/2006 | Viola et al. | EP | 0634144 | | 1/1995 |
| 2006/0278880 A1 | 12/2006 | Viola et al. | EP | 0646356 | A2 | 4/1995 |
| 2006/0289602 A1 | 12/2006 | Wales et al. | EP | 0646357 | A1 | 4/1995 |
| 2007/0027469 A1 | 2/2007 | Smith et al. | EP | 0669104 | A1 | 8/1995 |
| 2007/0034666 A1 | 2/2007 | Holsten et al. | EP | 0679367 | A2 | 11/1995 |
| 2007/0034668 A1 | 2/2007 | Holsten et al. | EP | 0392547 | B1 | 12/1995 |
| 2007/0045379 A1 | 3/2007 | Shelton | EP | 0685204 | A1 | 12/1995 |
| 2007/0073340 A1 | 3/2007 | Shelton, IV et al. | EP | 0699418 | A1 | 3/1996 |
| 2007/0075114 A1 | 4/2007 | Shelton, IV et al. | EP | 0702937 | A1 | 3/1996 |
| 2007/0083234 A1 | 4/2007 | Shelton, IV et al. | EP | 0705571 | A1 | 4/1996 |
| 2007/0084897 A1 | 4/2007 | Shelton, IV et al. | EP | 0484677 | B2 | 6/1996 |
| 2007/0102452 A1 | 5/2007 | Shelton, IV et al. | EP | 0541987 | B1 | 7/1996 |
| 2007/0102453 A1 | 5/2007 | Morgan et al. | EP | 0667119 | B1 | 7/1996 |
| 2007/0102472 A1 | 5/2007 | Shelton, IV | EP | 0770355 | A1 | 5/1997 |
| 2007/0102473 A1 | 5/2007 | Shelton, IV et al. | EP | 0625335 | B1 | 11/1997 |
| 2007/0102474 A1 | 5/2007 | Shelton, IV et al. | EP | 0552423 | | 1/1998 |
| 2007/0102475 A1 | 5/2007 | Ortiz et al. | EP | 0592244 | B1 | 1/1998 |
| 2007/0102476 A1 | 5/2007 | Shelton, IV et al. | EP | 0648476 | B1 | 1/1998 |
| 2007/0106317 A1 | 5/2007 | Shelton, IV et al. | EP | 0603472 | B1 | 11/1998 |
| 2007/0158385 A1 | 7/2007 | Hueil et al. | EP | 0878169 | A1 | 11/1998 |
| 2007/0170225 A1 | 7/2007 | Shelton, IV et al. | EP | 0760230 | B1 | 2/1999 |
| 2007/0175949 A1 | 8/2007 | Shelton, IV et al. | EP | 0537572 | B1 | 6/1999 |
| 2007/0175950 A1 | 8/2007 | Shelton, IV et al. | EP | 0552050 | B1 | 5/2000 |
| 2007/0175951 A1 | 8/2007 | Shelton, IV et al. | EP | 1090592 | A1 | 4/2001 |
| 2007/0175952 A1 | 8/2007 | Shelton, IV et al. | EP | 1256318 | B1 | 5/2001 |
| 2007/0175953 A1 | 8/2007 | Shelton, IV et al. | EP | 0908152 | B1 | 1/2002 |
| 2007/0175955 A1 | 8/2007 | Shelton, IV et al. | EP | 0872213 | B1 | 5/2002 |
| 2007/0175956 A1 | 8/2007 | Swayze et al. | EP | 1238634 | A2 | 9/2002 |
| 2007/0175957 A1 | 8/2007 | Shelton, IV et al. | EP | 0656188 | B1 | 1/2003 |
| 2007/0175958 A1 | 8/2007 | Shelton, IV et al. | EP | 0829235 | B1 | 6/2003 |
| 2007/0175959 A1 | 8/2007 | Shelton, IV et al. | EP | 0813843 | B1 | 10/2003 |
| 2007/0175960 A1 | 8/2007 | Shelton, IV et al. | EP | 0705570 | B1 | 4/2004 |
| 2007/0175962 A1 | 8/2007 | Shelton, IV et al. | EP | 1086713 | B1 | 5/2004 |
| 2007/0175964 A1 | 8/2007 | Shelton, IV et al. | EP | 1426012 | A1 | 6/2004 |
| 2007/0179476 A1 | 8/2007 | Shelton, IV et al. | EP | 0888749 | B1 | 9/2004 |
| 2007/0181632 A1 | 8/2007 | Milliman | EP | 1477119 | A1 | 11/2004 |
| 2007/0194079 A1 | 8/2007 | Hueil et al. | EP | 1479345 | A1 | 11/2004 |
| 2007/0194080 A1 | 8/2007 | Swayze et al. | EP | 1479347 | A1 | 11/2004 |
| 2007/0194081 A1 | 8/2007 | Hueil et al. | EP | 1479348 | A1 | 11/2004 |
| 2007/0194082 A1 | 8/2007 | Morgan et al. | EP | 1520523 | A1 | 4/2005 |
| 2007/0233053 A1 | 10/2007 | Shelton, IV et al. | EP | 1522264 | A1 | 4/2005 |
| 2007/0262116 A1 | 11/2007 | Hueil et al. | EP | 1550408 | A1 | 7/2005 |
| 2007/0295780 A1 | 12/2007 | Shelton et al. | EP | 1557129 | A1 | 7/2005 |
| 2008/0029570 A1 | 2/2008 | Shelton et al. | EP | 1064883 | B1 | 8/2005 |
| 2008/0029571 A1 | 2/2008 | Shelton et al. | EP | 1621141 | A2 | 2/2006 |
| 2008/0029572 A1 | 2/2008 | Shelton et al. | EP | 1520525 | A1 | 4/2006 |
| 2008/0029573 A1 | 2/2008 | Shelton et al. | EP | 1652481 | A2 | 5/2006 |
| 2008/0029574 A1 | 2/2008 | Shelton et al. | EP | 1382303 | B1 | 6/2006 |
| 2008/0029575 A1 | 2/2008 | Shelton et al. | EP | 1045672 | B1 | 8/2006 |
| 2008/0029576 A1 | 2/2008 | Shelton et al. | EP | 1617768 | B1 | 8/2006 |
| 2008/0029577 A1 | 2/2008 | Shelton et al. | EP | 1702567 | A2 | 9/2006 |
| 2008/0035701 A1 | 2/2008 | Racenet et al. | EP | 1129665 | B1 | 11/2006 |
| 2008/0041916 A1 | 2/2008 | Milliman et al. | EP | 1256317 | B1 | 12/2006 |
| 2008/0041917 A1 | 2/2008 | Racenet et al. | EP | 1728473 | A1 | 12/2006 |
| 2008/0078802 A1 | 4/2008 | Hess et al. | EP | 1728475 | A2 | 12/2006 |
| 2008/0082124 A1 | 4/2008 | Hess et al. | EP | 1479346 | B1 | 1/2007 |
| | | | EP | 1484024 | B1 | 1/2007 |
| FOREIGN PATENT DOCUMENTS | | | EP | 1300117 | B1 | 8/2007 |
| | | | FR | 1112936 | A | 3/1956 |
| CA | 2512960 A1 | 1/2006 | GB | 939929 | A | 10/1963 |
| CA | 2514274 A1 | 1/2006 | GB | 2336214 | A | 10/1999 |
| DE | 273689 C | 5/1914 | JP | 6007357 | A | 1/1994 |
| DE | 9412228 U | 9/1994 | JP | 7051273 | A | 2/1995 |
| DE | 69328576 T2 | 1/2001 | JP | 6033641 | A | 2/1996 |
| DE | 20112837 U1 | 10/2001 | JP | 6229050 | A | 9/1996 |
| DE | 20121753 U1 | 4/2003 | JP | 2001286477 A | | 10/2001 |
| DE | 10314072 A1 | 10/2004 | JP | 2002369820 A | | 12/2002 |
| EP | 0122046 A1 | 10/1984 | JP | 2005505322 T | | 2/2005 |
| EP | 0033548 B1 | 5/1986 | JP | 2005103293 A | | 4/2005 |
| EP | 0639349 A2 | 2/1994 | RU | 2187249 C2 | | 8/2002 |
| EP | 0593920 A1 | 4/1994 | RU | 2225170 C2 | | 3/2004 |

| | | | | | | | |
|---|---|---|---|---|---|---|---|
| SU | | 1377053 | A1 | 2/1988 | WO | WO 03/063694 A1 | 8/2003 |
| SU | | 1561964 | A1 | 5/1990 | WO | WO 03/077769 A1 | 9/2003 |
| SU | | 172476 | A1 | 3/1992 | WO | WO 03/082126 A1 | 10/2003 |
| SU | | 1722476 | A1 | 3/1992 | WO | WO 03/088845 A2 | 10/2003 |
| WO | WO 93/08755 | | A1 | 5/1993 | WO | WO 03/090630 A2 | 11/2003 |
| WO | WO 95/18572 | | A1 | 7/1995 | WO | WO 03/094743 A1 | 11/2003 |
| WO | WO 95/29639 | | | 11/1995 | WO | WO 03/094745 A1 | 11/2003 |
| WO | WO 96/35464 | | A1 | 11/1996 | WO | WO 03/094746 A1 | 11/2003 |
| WO | WO 98/30153 | | A1 | 7/1998 | WO | WO 03/094747 A1 | 11/2003 |
| WO | WO 99/12483 | | A1 | 3/1999 | WO | WO 03/101313 A1 | 12/2003 |
| WO | WO 99/15086 | | A1 | 4/1999 | WO | WO 03/105702 A2 | 12/2003 |
| WO | WO 99/34744 | | A1 | 7/1999 | WO | WO 2004/006980 A2 | 1/2004 |
| WO | WO 00/057796 | | A1 | 10/2000 | WO | WO 2004/032754 A2 | 4/2004 |
| WO | WO 00/72762 | | A1 | 12/2000 | WO | WO 2004/032760 A2 | 4/2004 |
| WO | WO 00/72765 | | A1 | 12/2000 | WO | WO 2004/032762 A1 | 4/2004 |
| WO | WO 01/05702 | | A1 | 1/2001 | WO | WO 2004/032763 A2 | 4/2004 |
| WO | WO 01/010482 | | A1 | 2/2001 | WO | WO 2004/047653 A2 | 6/2004 |
| WO | WO 01/62158 | | A2 | 8/2001 | WO | WO 2004/049956 A2 | 6/2004 |
| WO | WO 01/62162 | | A1 | 8/2001 | WO | WO 2004/086987 A1 | 10/2004 |
| WO | WO 01/62164 | | A2 | 8/2001 | WO | WO 2004/096057 A2 | 11/2004 |
| WO | WO 01/91646 | | A1 | 12/2001 | WO | WO 2004/112618 A2 | 12/2004 |
| WO | WO 02/17799 | | A1 | 3/2002 | WO | WO 2005/027983 A2 | 3/2005 |
| WO | WO 02/30297 | | A2 | 4/2002 | WO | WO 2005/096954 A2 | 10/2005 |
| WO | WO 02/043571 | | A2 | 6/2002 | WO | WO 2005/115251 A2 | 12/2005 |
| WO | WO 02/067785 | | A2 | 9/2002 | WO | WO 2006/044490 A2 | 4/2006 |
| WO | WO 02/098302 | | A1 | 12/2002 | WO | WO 2006/044581 A2 | 4/2006 |
| WO | WO 03/000138 | | A2 | 1/2003 | WO | WO 2006/044810 A2 | 4/2006 |
| WO | WO 03/001329 | | A2 | 1/2003 | WO | WO 2006/083748 A1 | 8/2006 |
| WO | WO 03/013363 | | A1 | 2/2003 | WO | WO 2006/132992 A1 | 12/2006 |
| WO | WO 03/020106 | | A2 | 3/2003 | WO | WO 2007/016290 A2 | 2/2007 |
| WO | WO 03/079909 | | A3 | 3/2003 | | | |
| WO | WO 03/030743 | | A2 | 4/2003 | | | |
| WO | WO 03/037193 | | A1 | 5/2003 | | | |
| WO | WO 2003/047436 | | A3 | 6/2003 | | | |
| WO | WO 03/057048 | | A1 | 7/2003 | | | |
| WO | WO 03/057058 | | A1 | 7/2003 | | | |

OTHER PUBLICATIONS

Disclosed Anonymously, "Motor-Driven Surgical Stapler Improvements," Research Disclosure Database No. 526041, Published: Feb. 2008.

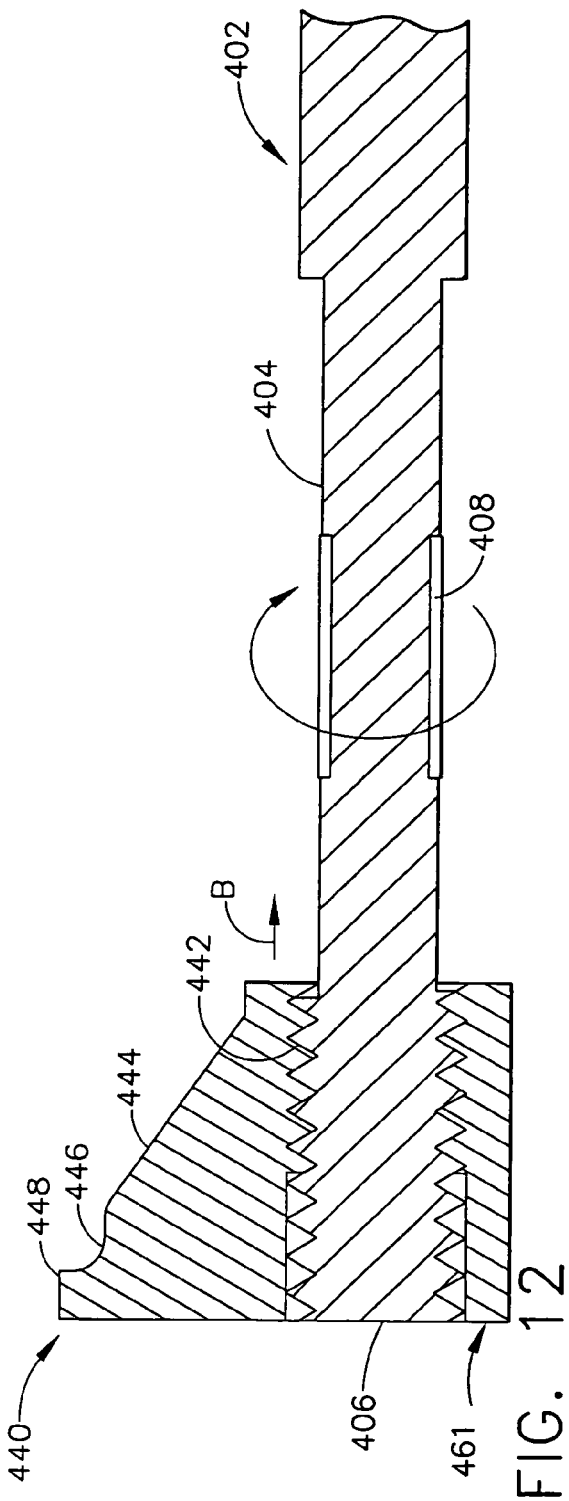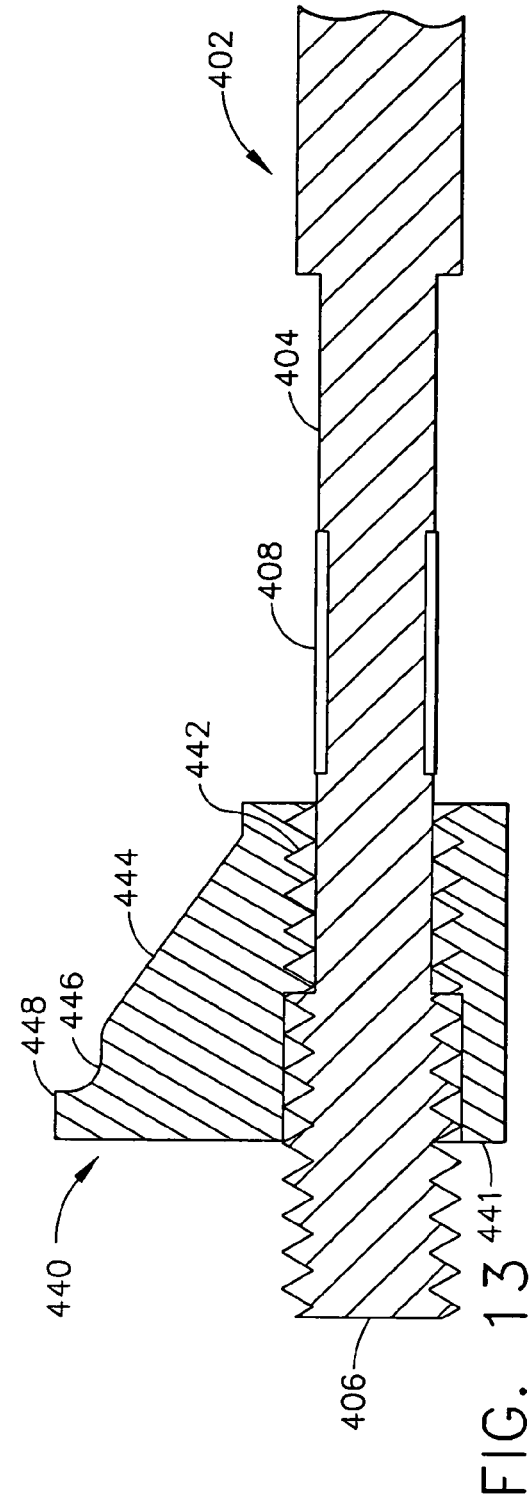

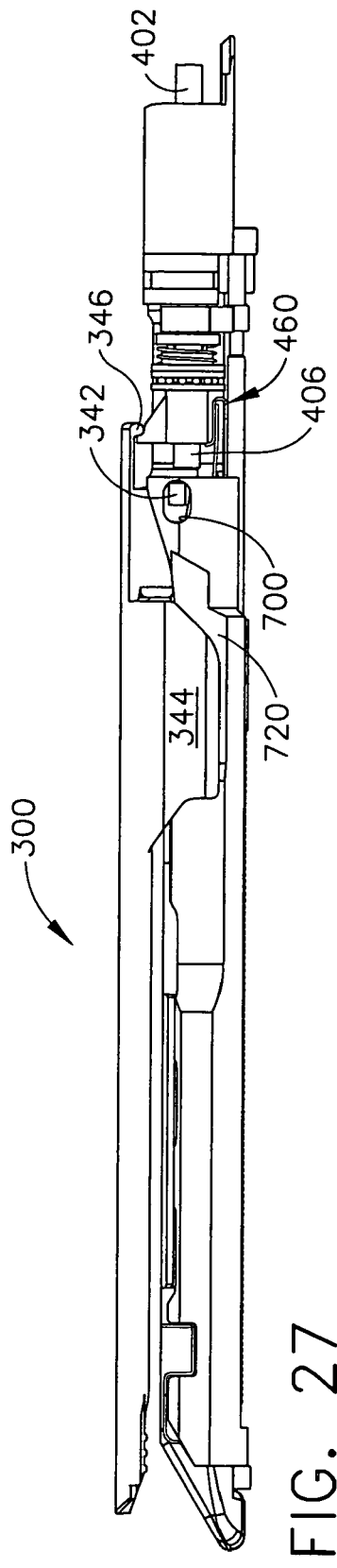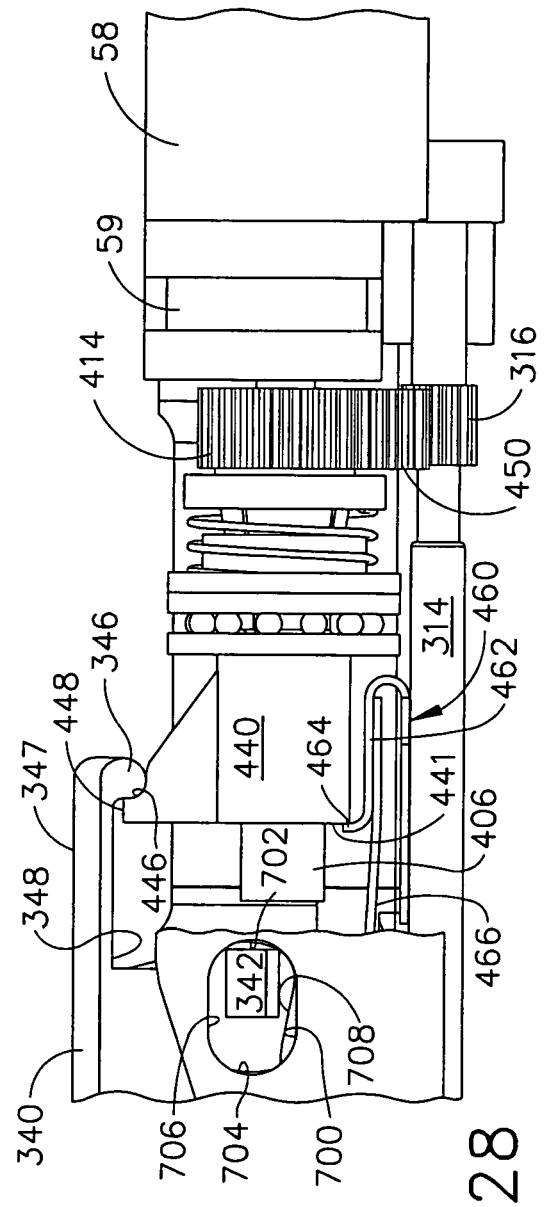

ELECTRO-MECHANICAL SURGICAL INSTRUMENT WITH CLOSURE SYSTEM AND ANVIL ALIGNMENT COMPONENTS

CROSS-REFERENCE TO RELATED APPLICATIONS

The present application is related to the following U.S. patent applications, which are incorporated herein by reference in their entirety:

Motor-Driven Surgical Cutting And Fastening Instrument With User Feedback System Inventors: Frederick E. Shelton, IV, John Ouwerkerk and Jerome R. Morgan (K&LG 050519/END5687USNP). application Ser. No. 11/343, 498, now U.S. Patent Publication No. 2007/0175958.

Motor-Driven Surgical Cutting And Fastening Instrument With Loading Force Feedback Inventors: Frederick E. Shelton, IV, John N. Ouwerkerk, Jerome R. Morgan, and Jeffrey S. Swayze, application Ser. No. 11/343,573, now U.S. Patent Publication No. 2007/0175952.

Motor-Driven Surgical Cutting And Fastening Instrument With Tactile Position Feedback Inventors: Frederick E. Shelton, IV, John N. Ouwerkerk, Jerome R. Morgan, and Jeffrey S. Swayze (K&LG 050515/END5693USNP), application Ser. No. 11/344,035, now U.S. Patent Publication No. 2007/0175962.

Motor-Driven Surgical Cutting And Fastening Instrument With Adaptive User Feedback Inventors: Frederick E. Shelton, IV, John N. Ouwerkerk, and Jerome R. Morgan (K&LG 050513/END5694USNP). application Ser. No. 11/343,447, now U.S. Patent Publication No. 2007/0175957.

Motor-Driven Surgical Cutting And Fastening Instrument With Articulatable End Effector Inventors: Frederick E. Shelton, IV and Christoph L. Gillum (K&LG050692/END5769USNP), application Ser. No. 11/343,562, now U.S. Patent Publication No. 2007/0175959.

Motor-Driven Surgical Cutting And Fastening Instrument With Mechanical Closure System Inventors: Frederick E. Shelton, IV and Christoph L. Gillum (K&LG 050693/END5770USNP), application Ser. No. 11/344,024, now U.S. Patent Publication No. 2007/0175953.

Surgical Cutting And Fastening Instrument With Closure Trigger Locking Mechanism Inventors: Frederick E. Shelton, IV and Kevin R. Doll (K&LG 050694/END5771USNP), Application Sel. No. 11/343,321, now U.S. Patent Publication No. 2007/0175955.

Gearing Selector For A Powered Surgical Cutting And Fastening Stapling Instrument Inventors: Frederick E. Shelton, IV, Jeffrey S. Swayze, Eugene L. Timperman (K&LG 050697/END5772USNP), application Ser. No. 11/343, 563, now U.S. Patent Publication No. 2007/0175951.

Surgical Instrument Having Recording Capabilities Inventors: Frederick E. Shelton, IV, John N. Ouwerkerk, and Eugene L. Timperman (K&LG 050698/END5773USNP), application Ser. No. 11/343,803, now U.S. Patent Publication No. 2007/0175964.

Surgical Instrument Having A Removable Battery Inventors: Frederick E. Shelton, IV, Kevin R. Doll, Jeffrey S. Swayze and Eugene Timperman (K&LG 050699/END5774USNP), application Ser. No. 11/344,020, now U.S. Patent Publication No. 2007/0175960.

Electronic Lockouts And Surgical Instrument Including Same Inventors: Jeffrey S. Swayze, Frederick E. Shelton, IV, Kevin R. Doll (K&LG 050700/END5775USNP), application Ser. No. 11/343,439, now U.S. Patent Publication No. 2007/0175956.

Endoscopic Surgical Instrument With A Handle That Can Articulate With Respect To The Shaft Inventors: Frederick E. Shelton, IV, Jeffrey S. Swayze, Mark S. Ortiz, and Leslie M. Fugikawa (K&LG 050701/END5776USNP), application Ser. No. 11/343,547, now U.S. Patent Publication No. 2007/0179476.

Disposable Staple Cartridge Having An Anvil With Tissue Locator For Use With A Surgical Cutting And Fastening Instrument And Modular End Effector System Therefor Inventors: Frederick E. Shelton, IV, Michael S. Cropper, Joshua M. Broehl, Ryan S. Crisp, Jamison J. Float, Eugene L. Timperman (K&LG 050703/END5778USNP). application Ser. No. 11/343,546, now U.S. Patent Publication No. 2007/0175950.

Surgical Instrument Having A Feedback System Inventors: Frederick E. Shelton, IV, Jerome R. Morgan, Kevin R. Doll, Jeffrey S. Swayze and Eugene Timperman (K&LG 050705/END5780USNP), application Ser. No. 11/343, 545, now U.S. Patent Publication No. 2007/0175949.

Articulatable Drive Shaft Arrangements For Surgical Cutting And Fastening Instruments Inventors: Frederick E. Shelton. IV and Christoph L. Gillum (K&LG 050692CON/END5769USCNT1), application Ser. No. 11/807,693, now U.S. Patent Publication No. 2007/0233053.

BACKGROUND

The present invention generally concerns surgical instruments and, more particularly, surgical cutting and fastening instruments.

Endoscopic surgical instruments are often preferred over traditional open surgical devices since a smaller incision tends to reduce the post-operative recovery time and complications. Generally, these endoscopic surgical instruments include an "end effector", a handle assembly and an elongated shaft that extends between the end effector and the handle assembly. The end effector is the portion of the instrument configured to engage the tissue in various ways to achieve a desired diagnostic or therapeutic effect (e.g., endocutter, grasper, cutter, staplers, clip applier, access device, drug/gene therapy delivery device, and energy device using ultrasound, RF, laser, etc.).

The end effector and the shaft portion are sized to be inserted through a trocar placed into the patient. The elongated shaft portion enables the end effector to be inserted to a desired depth and also facilitates some rotation of the end effector to position it within the patient. With judicious placement of the trocar and use of graspers, for instance, through another trocar, often this amount of positioning is sufficient. Surgical stapling and severing instruments, such as those described in U.S. Pat. No. 5,465,895, are examples of an endoscopic surgical instrument that successfully positions an end effector by insertion and rotation.

Over the years, various approaches have been taken by medical component manufacturers to reduce the overall cost of such endoscopic surgical instruments. While some of these approaches have been successful at addressing at least some of the user's needs, they still fall short of addressing other needs. For example, prior end effector designs employ an anvil that is pivotally coupled to a cartridge-supporting channel such that, when tissue is clamped between the anvil and the cartridge, the anvil tends to undesirably "roll" the tissue out of the desired position, making it difficult for the surgeon to precisely clamp the tissue in the desired position. Those approaches and others also employ mostly machined components which are more costly to manufacture and thus inflate the overall costs of the instrument.

Consequently there is a need for an end effector arrangement for a surgical cutting and fastening instrument that addresses the above-mentioned concerns by providing end effectors that are equipped with anvils that can close onto the channel in a substantially parallel fashion and which do not necessarily require the use of all machined components.

SUMMARY

In one general aspect, the present invention is directed to a surgical cutting and fastening instrument that comprises a control handle that has an elongate channel coupled thereto that is sized to support a cartridge therein. An anvil is pivotally coupled to the elongate channel such that the anvil is axially and laterally movable thereon and selectively pivotable between open and closed positions relative thereto. A drive system and closure nut are operably supported in the elongate channel. The closure nut is responsive to separate opening and closing motions from the drive system and coacts with the anvil such that upon receiving a closing motion from the drive system, said closure nut pulls the anvil to cause the anvil to close and axially move to an aligned position. The closure nut also causes the anvil to move to an open position upon application of an opening motion to the closure nut.

In another general aspect, the present invention is directed to a surgical cutting and fastening instrument that comprises a control handle and an elongate channel that is coupled to the control handle and is sized to support a cartridge therein. An anvil is pivotally coupled to the elongate channel such that the anvil is axially and laterally movable thereon and selectively pivotable between open and closed positions relative thereto. A closure wedge is supported on a drive member that operably extends into a portion of the elongate channel. The drive member is controlled by a control system in the control handle and is axially movable relative to the elongate channel such that upon application of a closing motion to the drive member, the drive member causes the closure wedge to apply a pulling force to the anvil to cause the anvil to move to a closed position wherein the anvil is aligned relative to the elongate channel and, upon application of an opening motion to the drive member, the closure wedge causes the anvil to move to an open position.

In another general aspect, the present invention is directed to a surgical cutting and fastening instrument that comprises control means and means for supporting a cartridge that is attached to the control means. An anvil is pivotally coupled to the means for supporting such that the anvil is axially and laterally movable thereon and is selectively pivotable between open and closed positions relative thereto. A drive means is supported in the means for supporting. The drive means selectively applies a pulling force to the anvil to cause the anvil to close and move to an aligned position relative to the means for supporting. The drive means also selective applies a pushing force to the anvil to cause the anvil to move to an open position relative to the means for supporting.

DRAWINGS

Various embodiments of the present invention are described herein by way of example in conjunction with the following figures, wherein like numerals may be used to describe like parts and wherein:

FIG. 12 is a cross-sectional view of the distal drive shaft portion and closure nut with the closure nut in an open position;

FIG. 13 is another cross-sectional view of the distal drive shaft portion and closure nut with the closure nut in the closed position;

FIG. 27 is a side elevational view of various end effector embodiments of the present invention in a closed position;

FIG. 28 is an enlarged partial cut away view of the end effector of FIG. 27;

DETAILED DESCRIPTION

Figure 1:
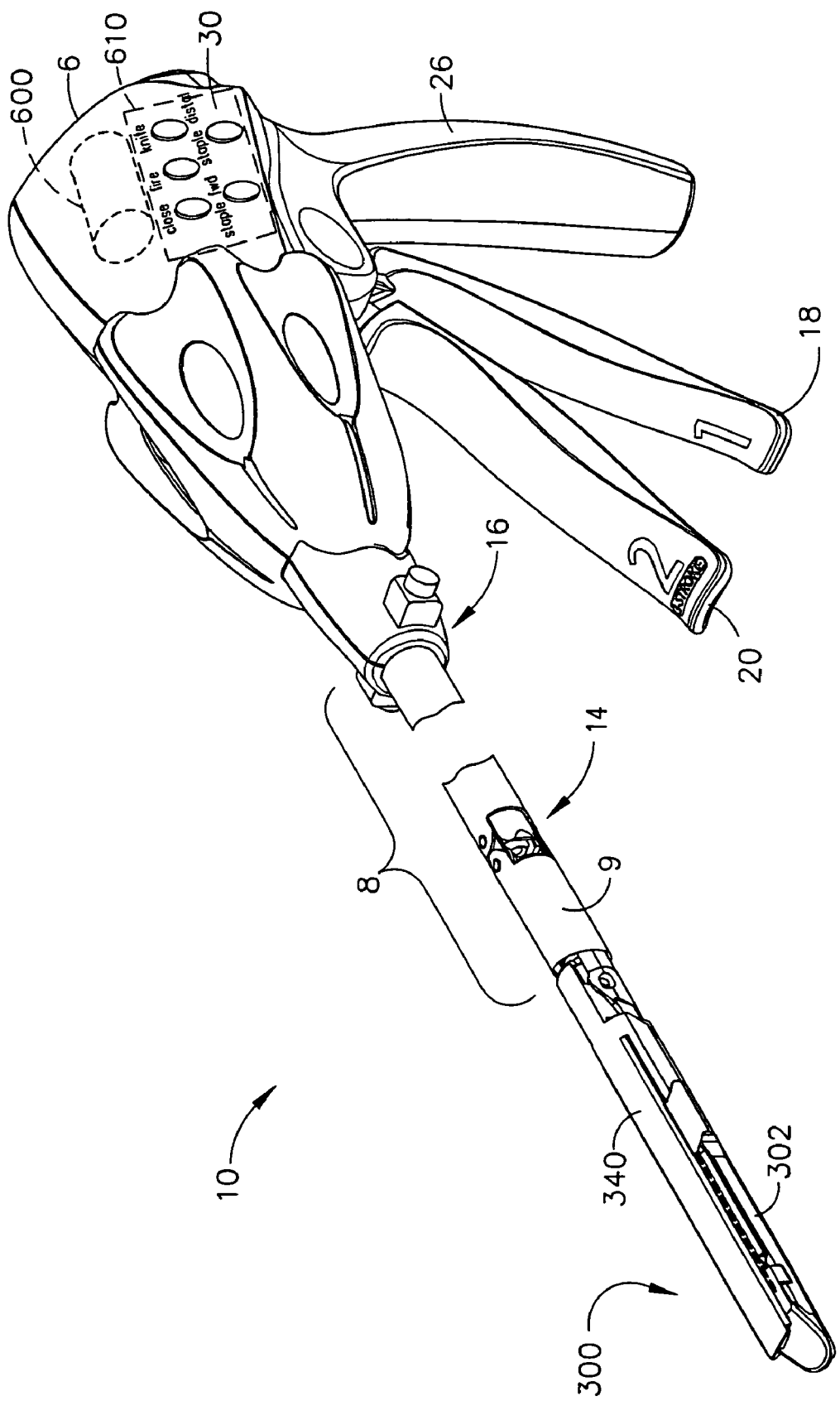
FIG. 1 is a perspective view of a surgical cutting and fastening instrument that can employ various end effector embodiments and staple cartridge embodiments of the present invention.
Figure 2:
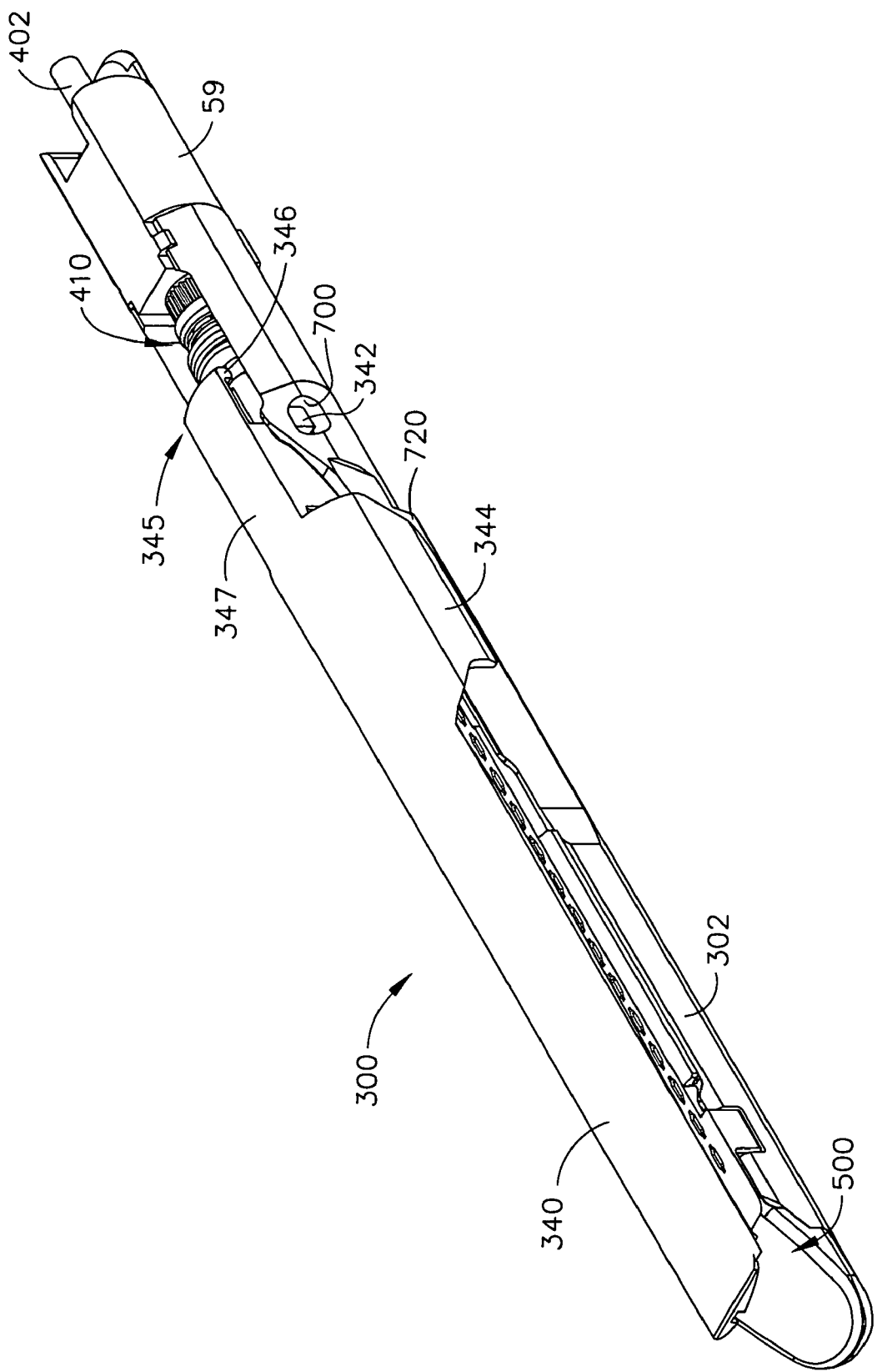
FIG. 2 is a perspective view of an end effector embodiment of the present invention in a closed position.
Figure 3:
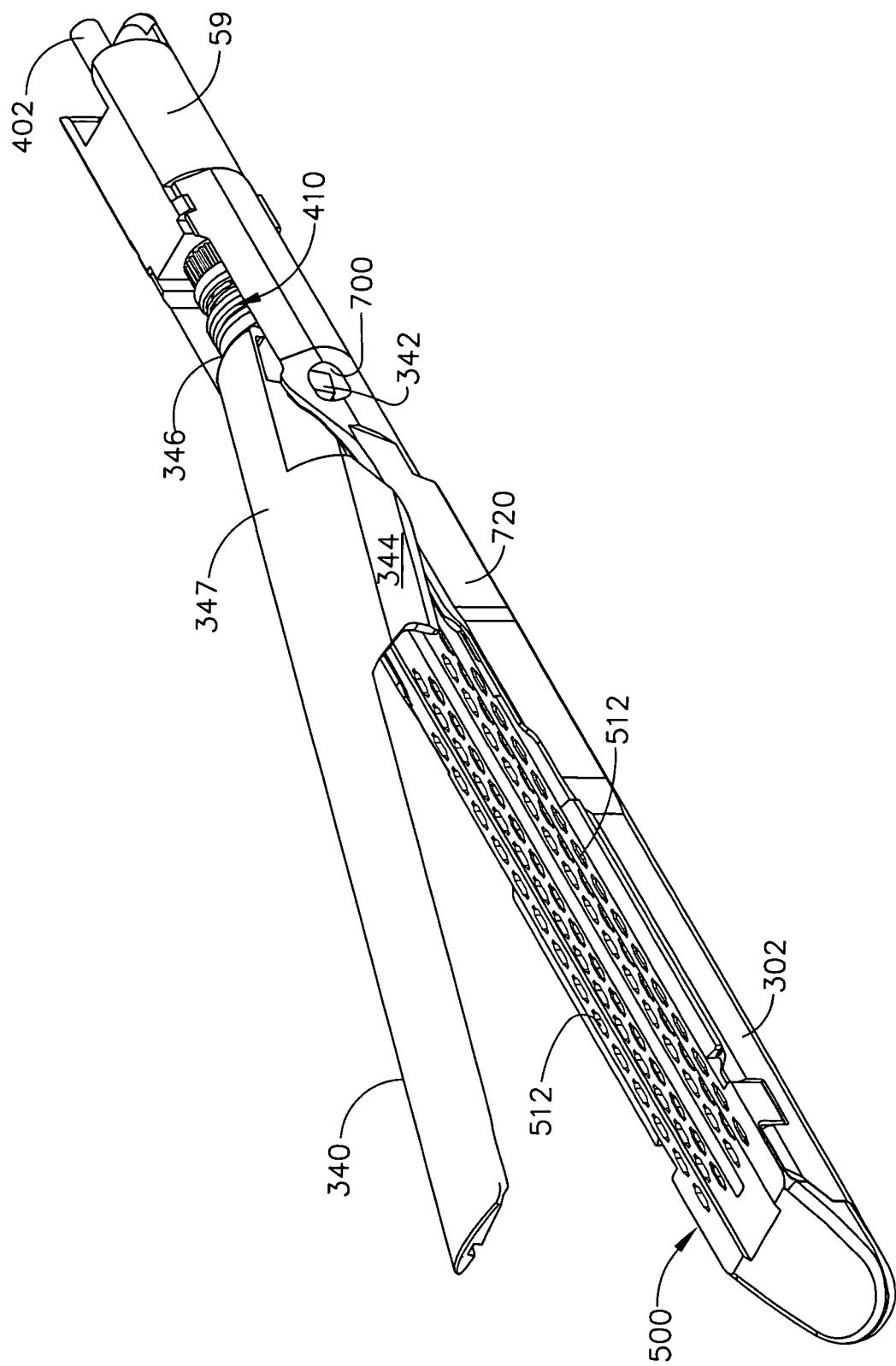
FIG. 3 is a perspective view of the end effector of FIG. 2 in an open position.
Figure 4:
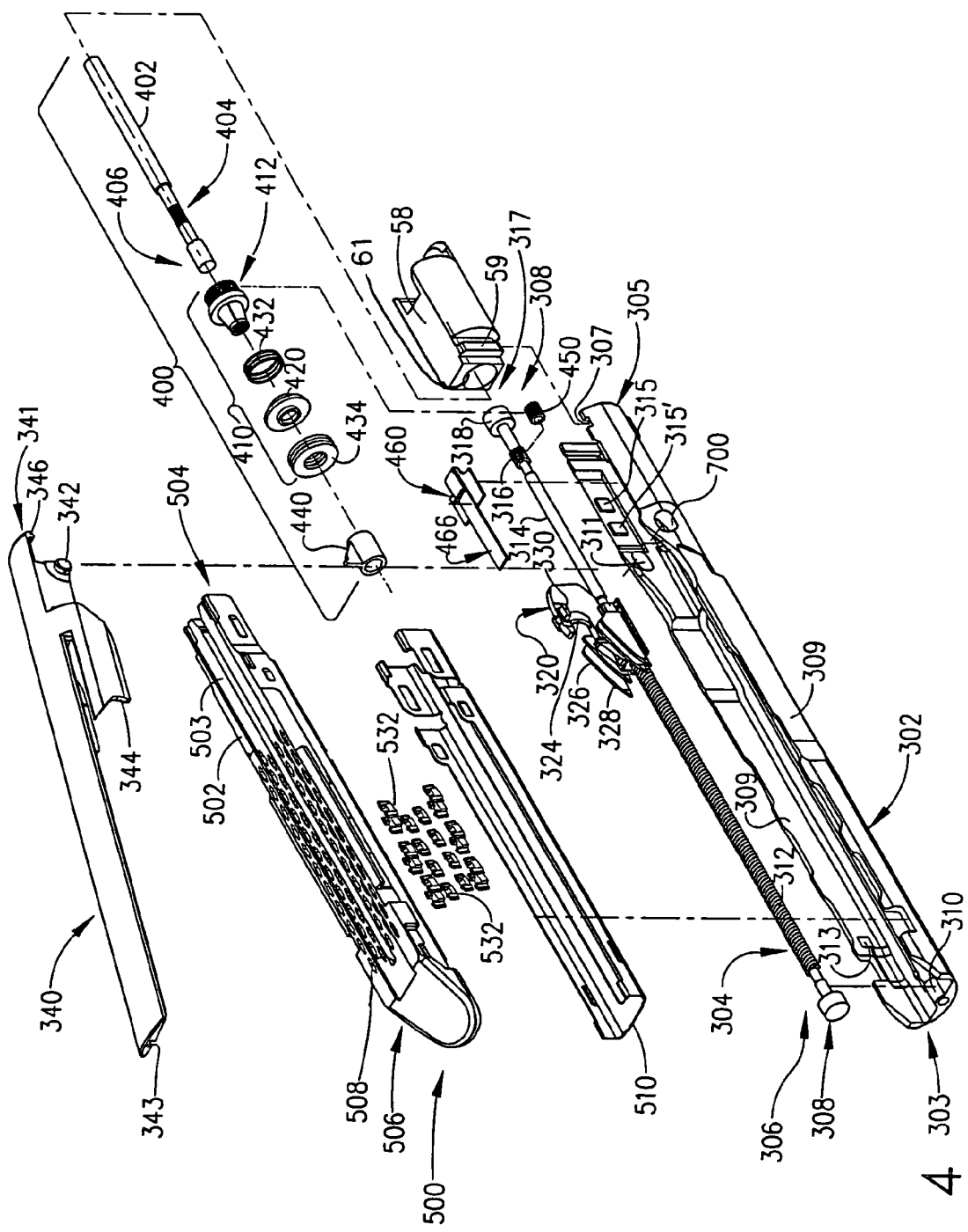
FIG. 4 is an exploded assembly view of an end effector embodiment of the present invention.
Figure 5:
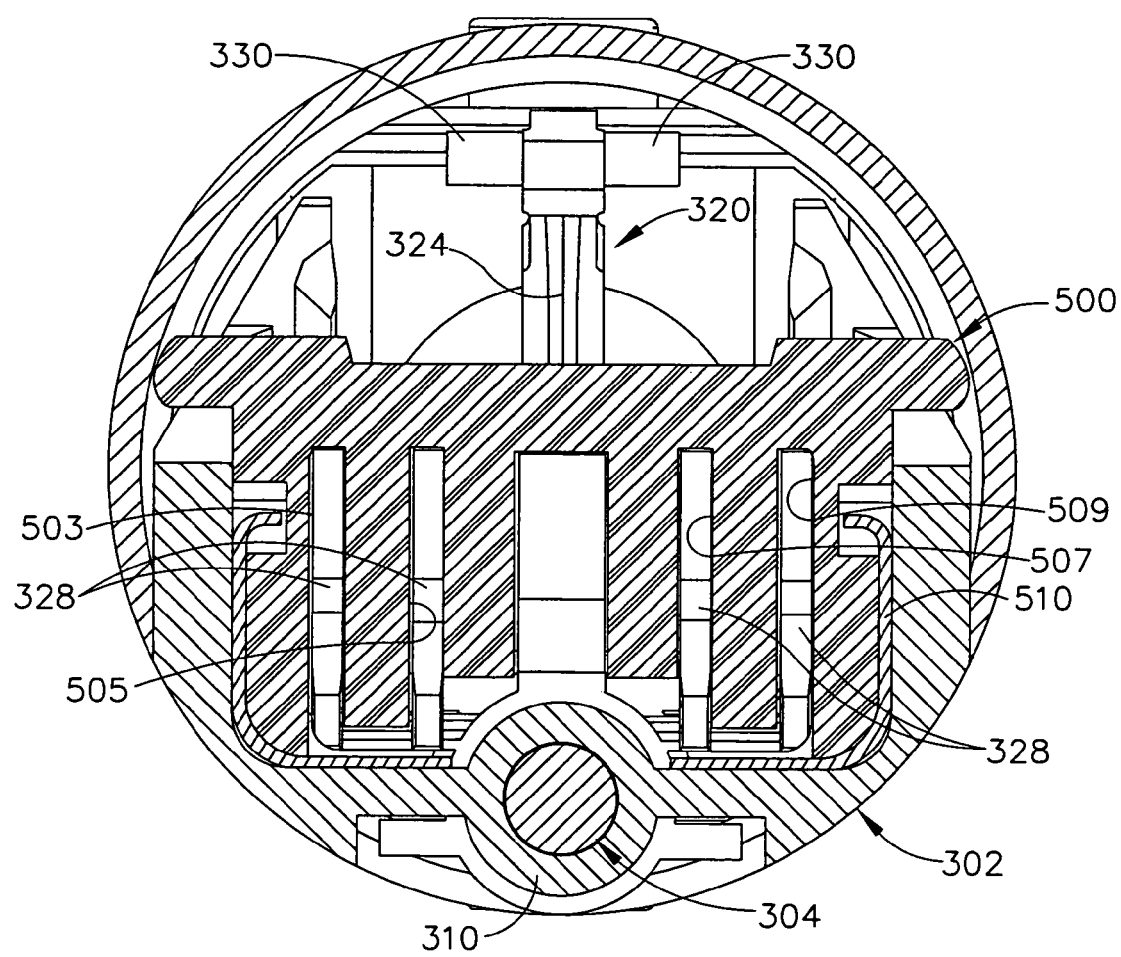
FIG. 5 is a cross sectional view of an end effector embodiment of the present invention supporting a staple cartridge therein with some of the components thereof omitted for clarity.

FIG. 1 depicts a surgical cutting and fastening instrument 10 that is capable of practicing various unique benefits of the end effectors and drive arrangements of the present invention. The surgical instrument 10 depicted in FIG. 1 comprises a handle 6, a shaft assembly 8, and an articulating end effector 300 pivotally connected to the shaft assembly 8 at an articulation pivot 14. In various embodiments, the control handle houses a drive motor 600 and control system generally represented as 610 therein for controlling the opening and closing of the end effector 300 and the cutting and stapling of the tissue clamped therein. An articulation control 16 may be provided adjacent to the handle 6 to effect rotation of the end effector 300 about the articulation pivot 14. The handle 6 of the instrument 10 may include a closure trigger 18 and a firing trigger 20 for actuating the end effector 300. The end effector 300 is shown separated from the handle 6 preferably by an elongate shaft 8. In one embodiment, a clinician or operator of the instrument 10 may articulate the end effector 300 relative to a proximal portion of the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein in its entirety by reference. Other articulation arrangements could also be employed.

As will be discussed in further detail below, various end effector embodiments include an anvil 340, which is maintained at a spacing that assures effective stapling and severing of tissue clamped in the end effector 300. In various exemplary embodiments, the handle 6 may include a pistol grip 26 towards which a closure trigger 18 is pivotally drawn by the clinician to cause clamping or closing of the anvil 340 toward cartridge 500 seated in an elongate channel 302 of the end effector 300 to thereby clamp tissue positioned between the anvil 340 and the staple cartridge 500. A firing trigger 20 may be situated farther outboard of the closure trigger 18. In various embodiments, once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 300. Those of ordinary skill in the art will readily appreciate however, that other handle and drive system arrangements may be successfully employed in connection with various embodiments described herein and their equivalent structures without departing from the spirit and scope of the present invention.

It will be appreciated that the terms "proximal" and "distal" are used herein with reference to a clinician gripping the handle 6 of an instrument 10. Thus, the end effector 300 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

FIGS. 1-5 illustrate a unique and novel end effector 300 of various embodiments of the present invention adapted for use with a staple cartridge 500, the basic operation of which is known in the art. For example, U.S. Pat. No. 6,978,921, entitled "Surgical Stapling Instrument Incorporating an E-beam Firing Mechanism," which is incorporated herein by reference in its entirety, provides more details about the construction of such staple cartridges.

Figure 6:
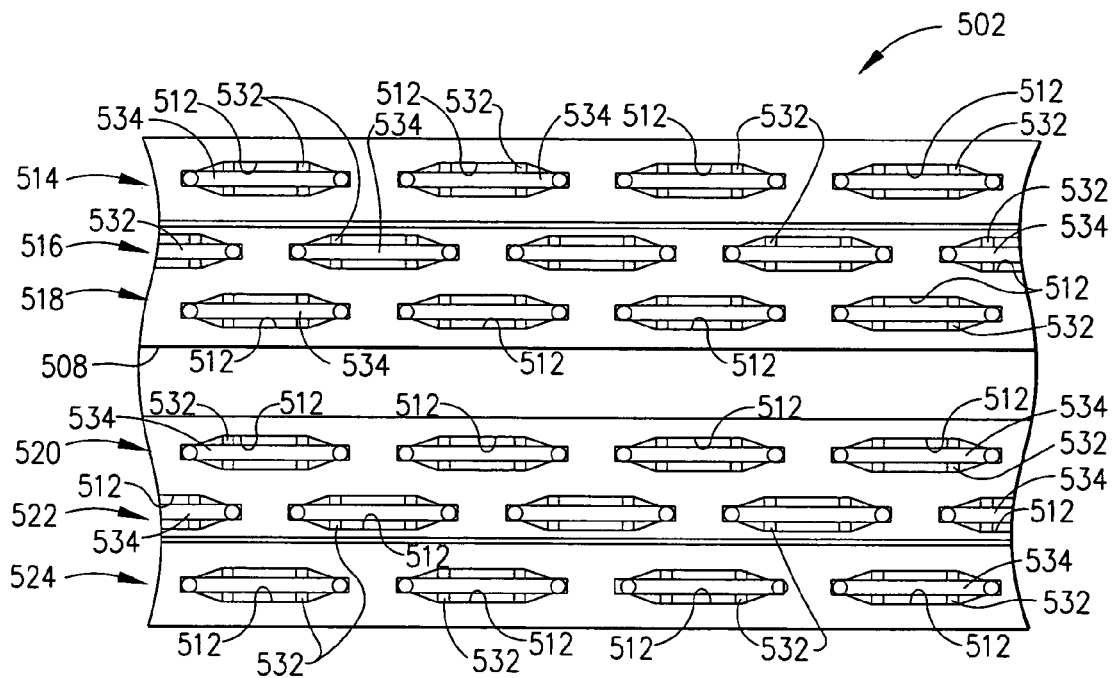
FIG. 6 is a partial top view of a staple cartridge that may be employed in connection with various embodiments of the present invention.

In general, such staple cartridges 500 include a cartridge body 502 that is divided by a central, elongated slot 508 which extends from the proximal end 504 of the cartridge body 502 towards its tapered outer tip 506. See FIG. 4. The cartridge body 502 may be fabricated from a polymeric material and be attached to a metal cartridge pan 510. A plurality of staple-receiving pockets 512 are formed within the cartridge body 502 and are arranged in six laterally spaced longitudinal rows or "lines" of staples 514, 516, 518, 520, 522, 524. See FIG. 6. Positioned within the pockets 512 are staple-supporting drivers 532 which support staples 534 thereon. Depending upon the location (line) of staple-receiving pockets 512, the staple supporting drivers 532 may support one or two staples 530 thereon. The cartridge body 502 further includes four longitudinal slots 503, 505, 507, 509 extending from its proximal end 504 to its tapered outer tip 506 for receiving corresponding sled cams 328 formed on a wedge sled 326 in the end effector 300, the construction and operation of which will discussed in further detail below. See FIG. 5. As the sled cams 328 are advanced through their respective slots 503, 505, 507, 509 in the cartridge body 502 from proximal end 504 to distal end 506, they contact the staple-supporting drivers 532 associated with those slots and force the staple-supporting drivers 532 and the staples 534 that they support upward out of the cartridge body 502. See FIG. 7. As the ends of the legs 536 of the staple 534 contact the pockets 350 formed in the bottom surface 341 of the anvil 340, they are folded over to close the staples 534.

Various end effectors of the present invention include an elongate channel 302 that is sized to removably receive and support the cartridge body 502 and pan 510 of a disposable cartridge 500 therein. A knife screw 304 is rotatably supported in the elongate channel 302. The knife screw 304 has a distal end 306 that has a distal thrust bearing 308 attached thereto that is rotatably supported by a distal bearing housing 310 formed in the distal end 303 of the elongate channel 302. See FIG. 4. The knife screw 304 has a central drive portion 312 with a helical thread formed thereon. The knife screw 304 further has a smooth extension portion 314 and a knife screw gear 316 formed thereon or otherwise attached thereto. A proximal thrust bearing 318 is formed or attached to the proximal end 317 of the knife screw 304. The proximal thrust bearing 318 is rotatably housed within a proximal bearing housing 319 supported in a distal spine tube segment 58. The distal spine tube segment 58 has a pair of columns 59 formed on its distal end that are adapted to be received in vertical slots 307 formed in the proximal end 305 of the elongate channel 302. The columns 59 may be retained within the slots 307 in the elongate channel 302 by friction, adhesive, or by the distal end of the shaft tube 9. See FIGS. 1 and 4.

Various embodiments of the present invention further include a knife assembly 320 that has a knife/sled bearing 322 that is threaded onto the threaded portion 312 of the knife screw 304. The knife assembly 320 supports a vertically extending blade 324 and a wedge sled 326 that supports the four sled cams 328. The reader will understand that, as the knife screw 304 is rotated in a clockwise direction, the knife assembly 320 and the wedge sled 326 is advanced toward the distal end 303 (direction "A") of the elongate channel 302 and, when the knife screw 304 is rotated in a counterclockwise direction, the knife assembly 320 and wedge sled 326 is moved toward the proximal end 305 of the channel member 302 (direction "B"). In addition, the knife assembly 320 has a pair of laterally extending deflector tabs 330 protruding therefrom, the purpose of which will be discussed below.

Figure 7:
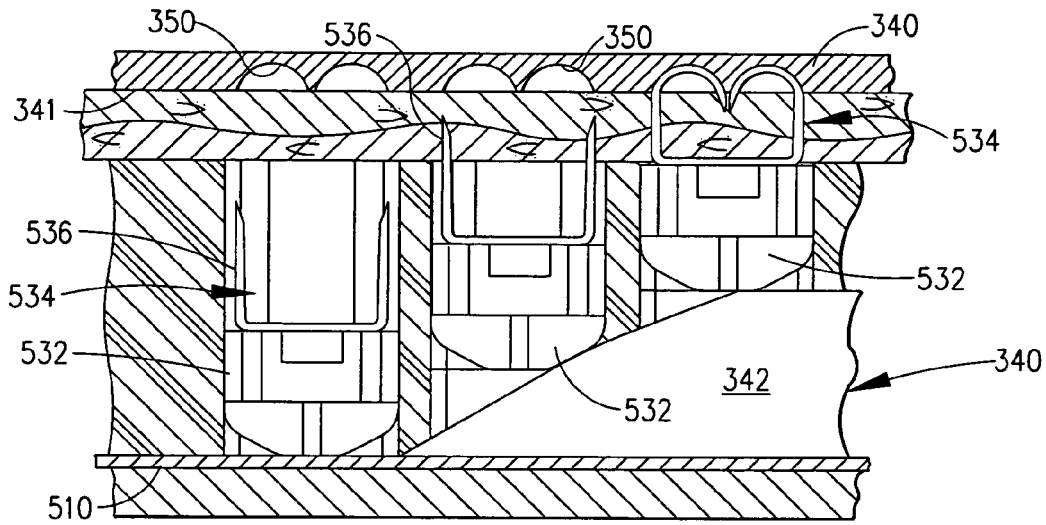
FIG. 7 is a partial cross-sectional view of a staple cartridge and end effector embodiment of the present invention illustrating the firing of staples into tissue clamped in the end effector.
Figure 31:
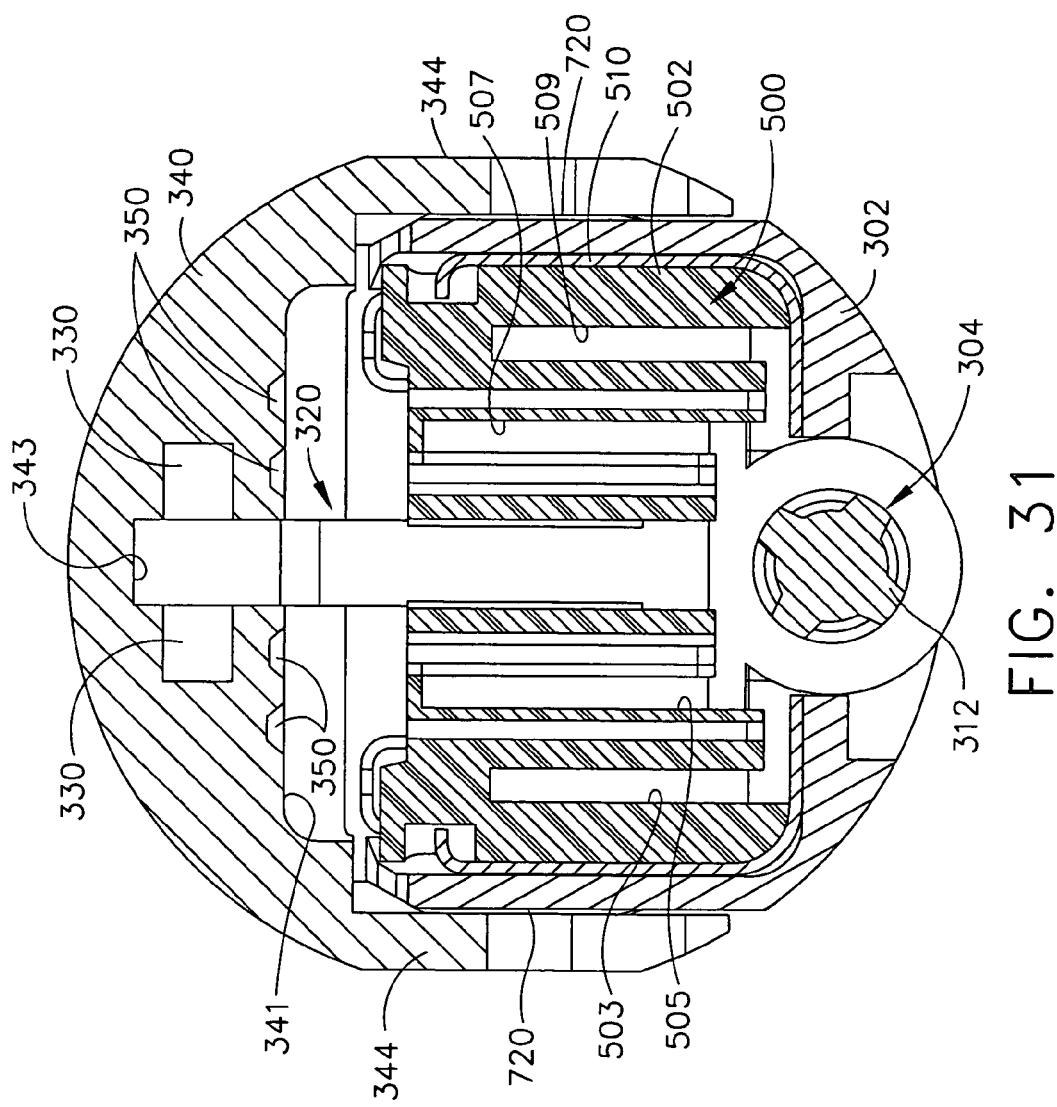
FIG. 31 is a cross-sectional view of the end effector of FIGS. 27-29.

In various embodiments of the present invention, an anvil 340 is pivotally coupled to the proximal end 305 of the channel member 302 by a pair of trunnion tabs 342 that are sized to be received in oval-shaped pivot holes 700 provided through the side walls 309 of the elongate channel 302. In various embodiments, the anvil 340 may be stamped from sheet metal or other material such that the trunnion tabs 342 are substantially rectangular or square shaped. In other embodiments, the anvil 340 may be molded or machined from other materials such that it is rigid in nature and the trunnion tabs or pins are substantially round. As can be seen in FIGS. 7 and 31, the bottom surface 341 of the anvil 340 has a series of staple forming pockets 350 formed therein. It will be understood that the staple forming pockets 350 serve to close the staples 534 as the ends of the staple legs 536 are forced into contact therewith. In addition, a longitudinal clearance slot 343 may be provided in the bottom surface 341 of the anvil 340 for receiving the upper end of the knife assembly 320 and the guide tabs 330 therethrough such that the laterally extending guide tabs 330 serve to urge the anvil 340 down onto the elongated channel 302 as the knife assembly 320 and wedge sled 326 are driven through the cartridge 500 to cut the tissue and deploy the staples 534.

A drive assembly for operating various embodiments of the end effector 300 will now be described. In various embodiments, a distal drive shaft portion 402 extends through a drive shaft hole 61 in the distal spine tube 58. See FIG. 4. The distal drive shaft portion 402 may extend directly to a drive motor arrangement 600 in the control handle 6 or it may be articulated to enable the end effector 300 to be pivoted relative to the shaft or closure tube assembly that connects the end effector 300 to the control handle 6.

Figure 8:
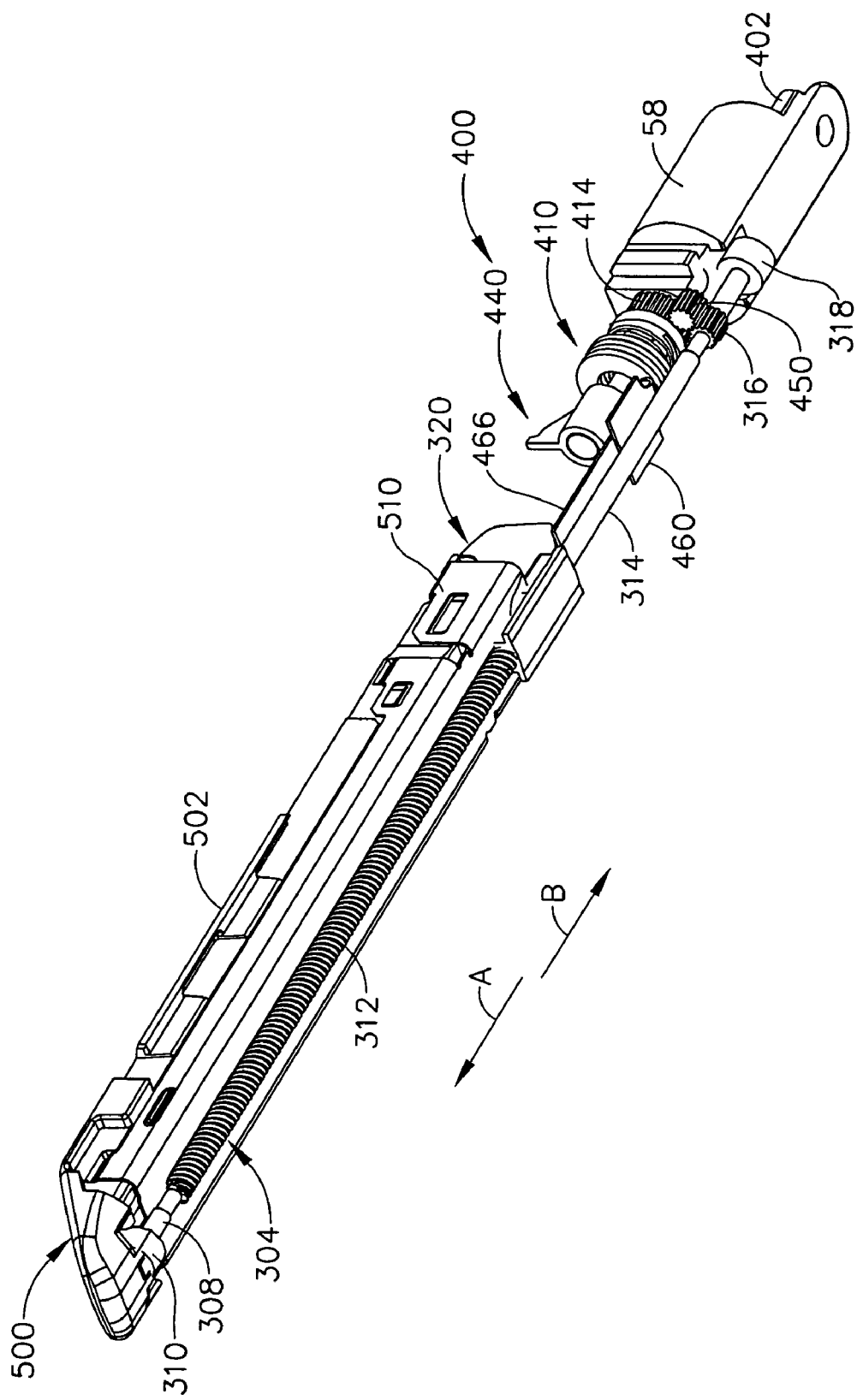
FIG. 8 is a bottom perspective view of a portion of an end effector embodiment of the present invention supporting a staple cartridge therein.
Figure 9:
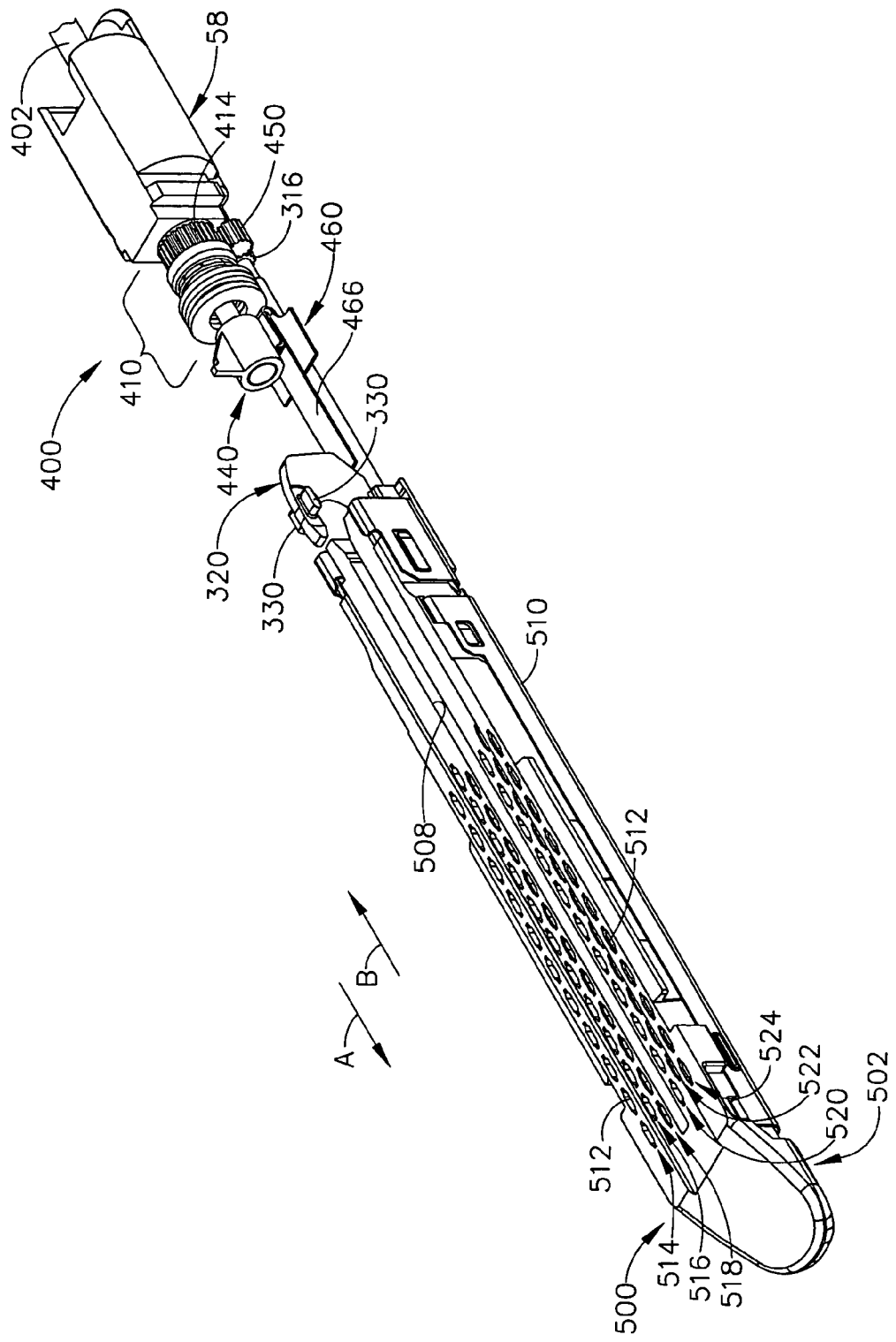
FIG. 9 is a partial perspective view of an end effector embodiment of the present invention supporting a staple cartridge therein.
Figure 10:
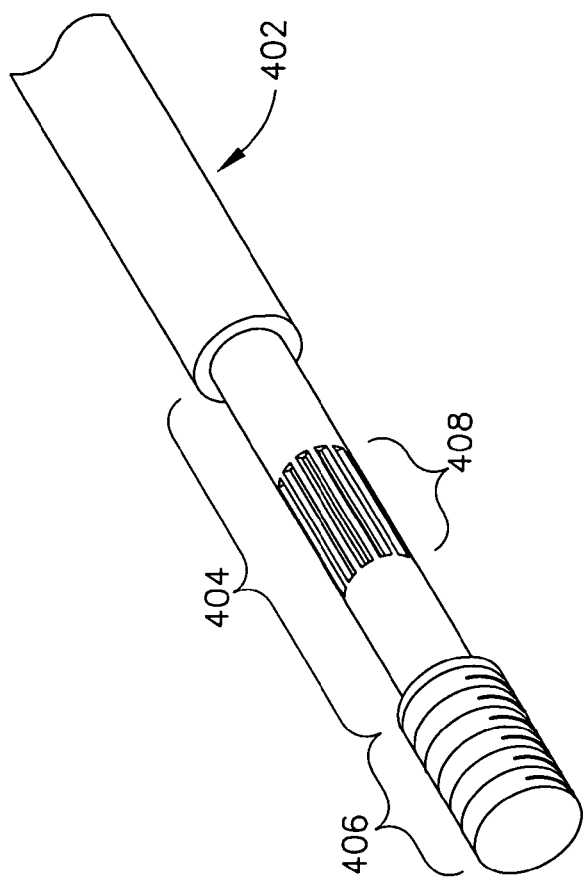
FIG. 10 is a perspective view of a distal drive shaft portion of various embodiments of the present invention.
Figure 11:
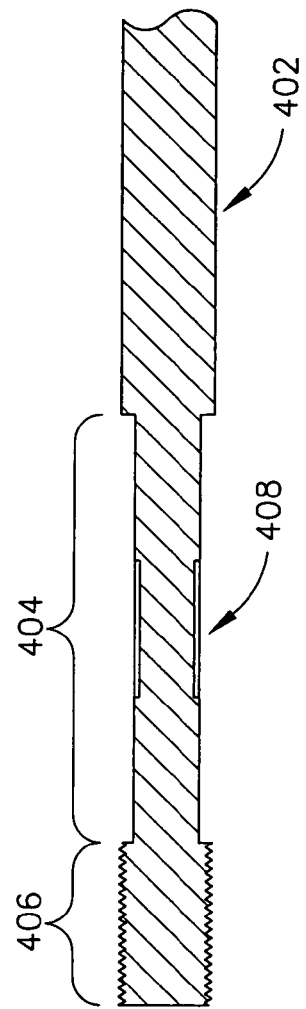
FIG. 11 is a cross-sectional view of the distal drive shaft portion of FIG. 10.
Figure 14:
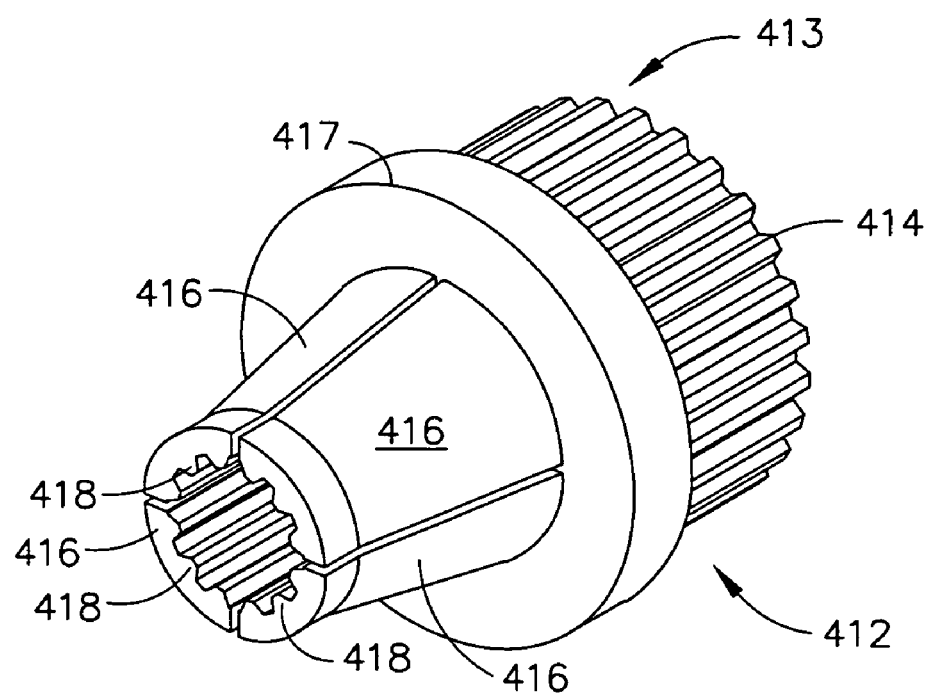
FIG. 14 is a perspective view of a tapered clutch member of various embodiments of the present invention.
Figure 15:
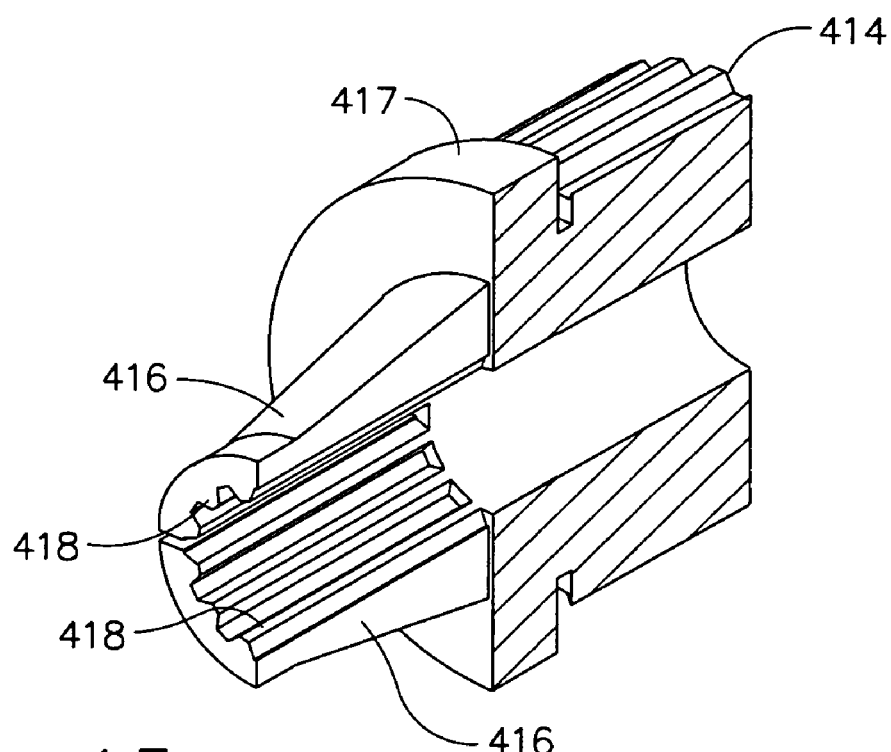
FIG. 15 is a cross-sectional view of the tapered clutch member of FIG. 14.

As can be seen in FIGS. 10-13, in various embodiments of the present invention the distal drive shaft portion 402 has a clutch-receiving portion 404 and a closure thread 406 formed thereon. A clutch assembly 410 is slidably received on the clutch-receiving portion 404 of the drive shaft portion 402. In various embodiments, the clutch assembly 410 includes a collet-like tapered clutch member 412 that has a drive gear 414 integrally formed on its proximal end 413. See FIGS. 14 and 15. The drive gear 414 meshes with a transfer gear 450 that in turn meshes with the knife screw gear 316. See FIGS. 8 and 9. Thus, when the clutch assembly 410 drivingly engages the distal drive shaft portion 402, the drive gear 414 rotates the transfer gear 450 which, in turn rotates the knife screw gear 316.

Figure 16:
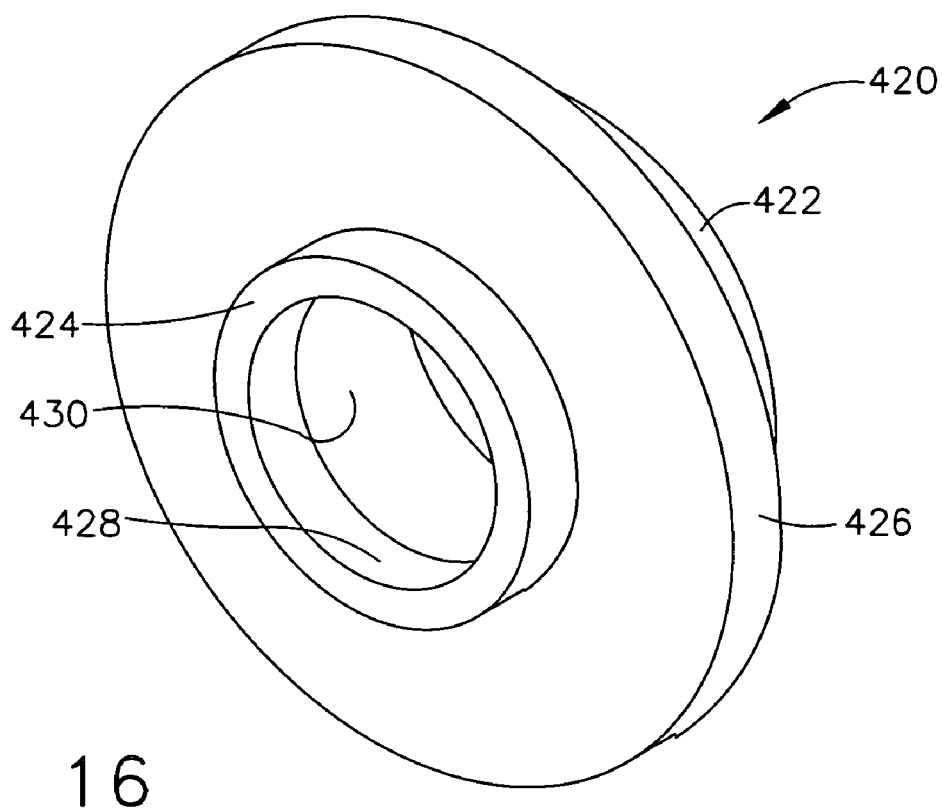
FIG. 16 is a perspective view of a clutch plate of various embodiments of the present invention.
Figure 17:
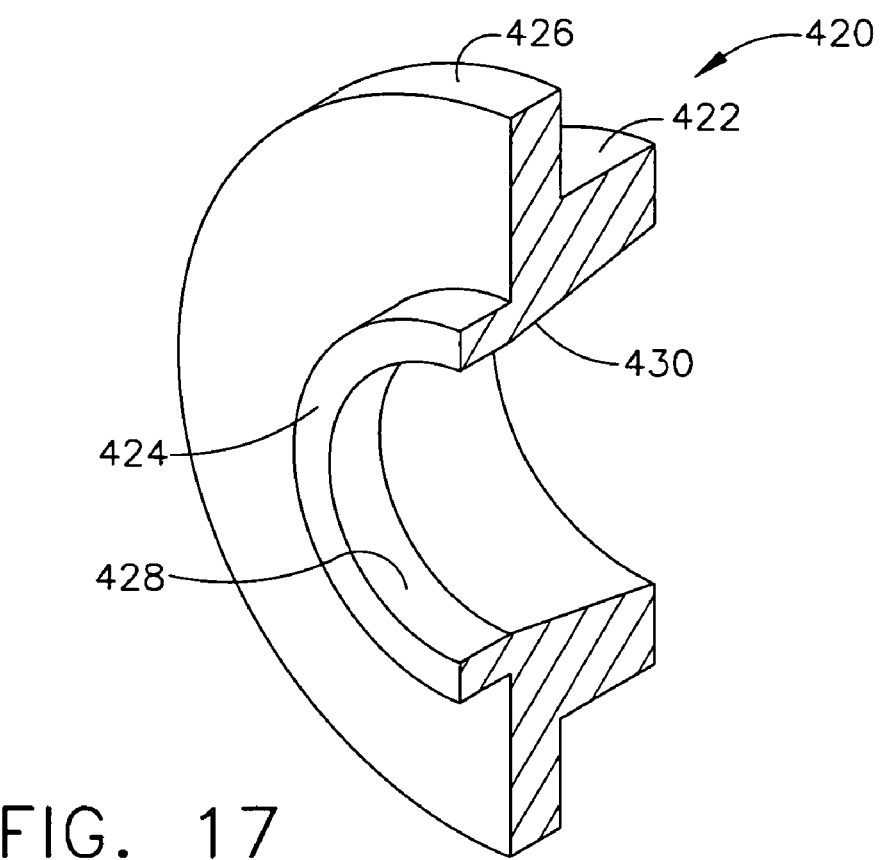
FIG. 17 is a cross-sectional view of the clutch plate of FIG. 16.
Figure 18:
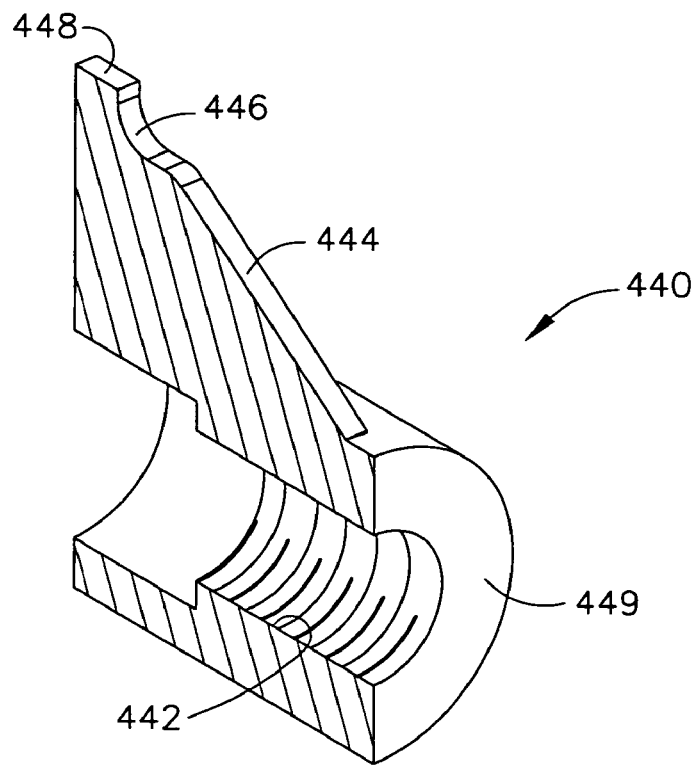
FIG. 18 is a perspective view of a closure nut of various embodiments of the present invention.
Figure 19:
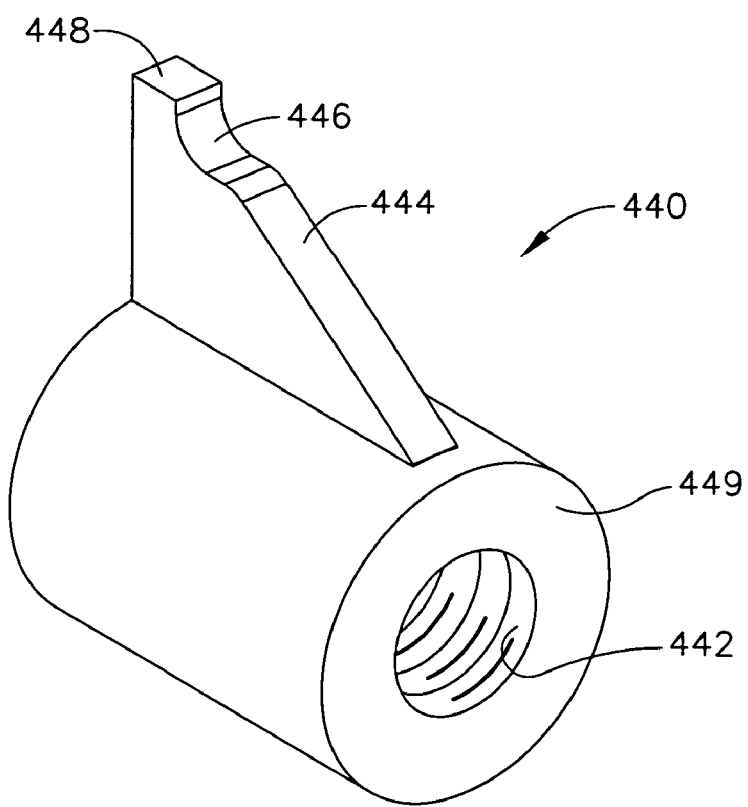
FIG. 19 is a cross-sectional view of the closure nut of FIG. 18.

A series of four tapered sections 416 are formed on the distal end 415 of the tapered clutch member 412. A series of male splines 418 are formed in the interior of the tapered sections 416. See FIGS. 14 and 15. The male splines 418 are adapted to selectively engage a female spline section 408 formed on the distal drive shaft portion 402 as will be discussed in further detail below. See FIGS. 10-13. The clutch assembly 410 further includes a clutch plate 420 that is received on the tapered sections 416 of the tapered clutch member 412. As can be seen in FIGS. 16 and 17, the clutch plate 420 has a proximal hub portion 422 and a distal hub portion 424 that is separated by a flange portion 426. A cylindrical distal hole portion 428 extends through the distal hub portion 424 and a tapered proximal hole 430 extends through the flange portion 426 and the proximal hub portion 422. The hole portions 428, 430 enable the clutch plate 420 to be slidably received on the drive shaft 402 and slide onto the tapered clutch member 412. A clutch opening spring 432 is provided between a flange portion 417 formed on the tapered clutch member 412 and the flange portion 426 of the clutch plate 420 and a thrust bearing 434 is also journaled on the clutch-receiving portion 404 adjacent to the clutch plate 420. See FIGS. 21 and 22.

Also in various embodiments, a closure nut 440 is received on the distal drive shaft portion 402. As can be seen in FIGS. 12, 13, 18 and 19, the closure nut 440 has a threaded hole portion 442 extending partially therethrough to enable it to be threaded onto the closure thread 406 on the distal drive shaft portion 402. As can be further seen in those Figures, the closure nut 440 has an upstanding closure ramp 444 protruding therefrom. The top of the closure ramp 444 terminates in a radiused portion 446 that extends to an upstanding closure tab 448 that is adapted to engage a downwardly protruding closure hook 346 formed on the proximal end 345 of anvil 340.

Figure 21:
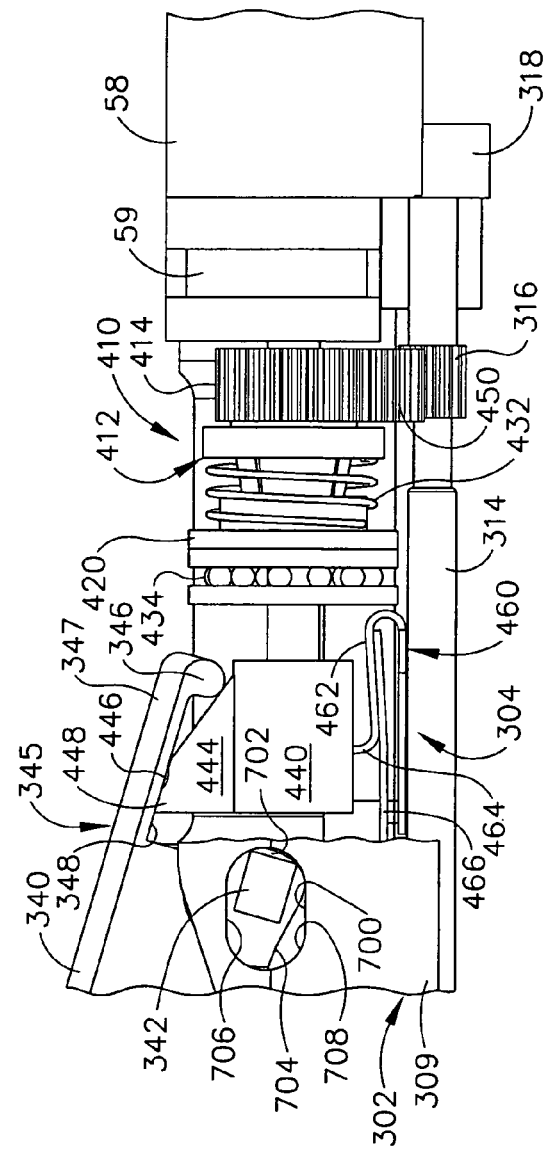
FIG. 21 is an enlarged partial cut away view of the end effector of FIG. 20.
Figure 22:
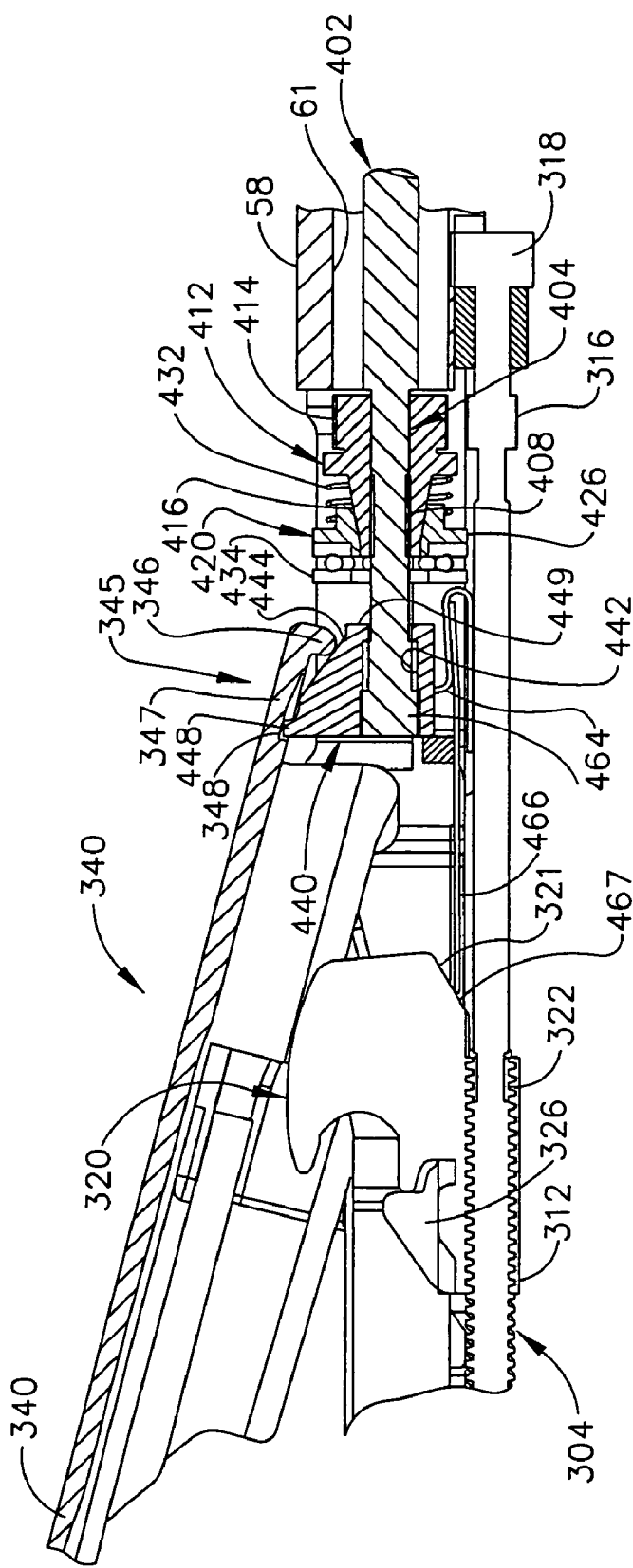
FIG. 22 is another enlarged partial cutaway view of the end effector of FIG. 20.

More specifically and with reference to FIG. 21, the proximal end 345 of the anvil 340 has an anvil closure arm portion 347 protruding proximally therefrom that terminates in a downwardly extending closure hook 346. As can also be seen in that Figure, the bottom surface of the anvil closure arm 347 has a tab relief groove 348 therein for receiving the closure tab 348 when the closure nut 440 is advanced to its most distal position (shown in FIGS. 27-30). Also in various embodiments, a closure lock spring 460 is attached to the bottom of the elongate channel 302, by mechanical fastener arrangements or adhesive. The closure lock spring 460 has an upper portion 462 that terminates in an upstanding retainer lip 464. In addition, longitudinally extending retainer arm 466 is rigidly attached to the upper portion 462 of the closure lock spring 460. See FIG. 4.

Figure 32:
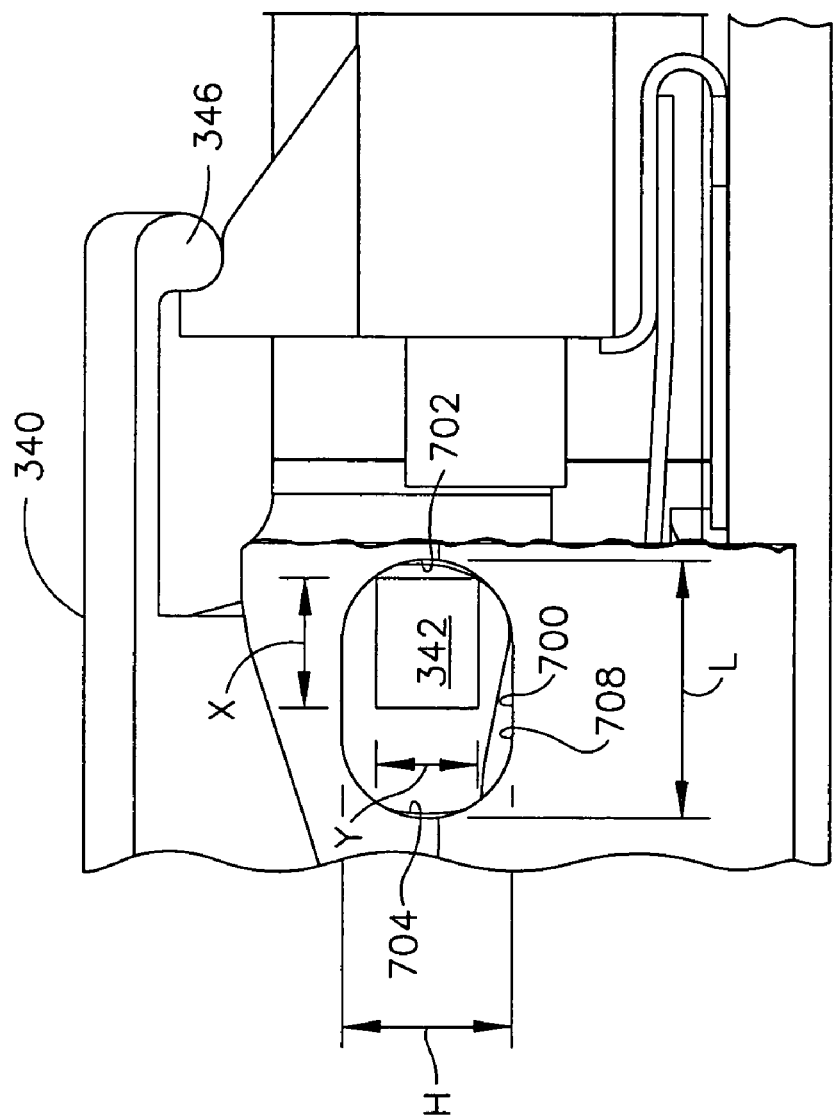
FIG. 32 is a partial enlarged view of a portion of an end effector of the present invention.

Various embodiments of the present invention employ an anvil 340 that is capable of moving axially and laterally relative to the elongate channel 302 prior to being advanced to the closed position. More specifically and with reference to FIGS. 20-30, in various embodiments, the elongate channel 302 is stamped or otherwise formed from sheet metal or the like and the pivot holes may be punched therein. Such construction leads to reduced manufacturing costs for the end effector. Other embodiments may be machined from rigid materials such as 416 stainless steel such that the trunnion pins are substantially round in cross-section. Regardless of which manufacturing method is employed to manufacture the anvil 340 and the resulting shape of the trunnion tabs 342, as can be seen in FIGS. 21, 24, 26, 28, and 32, the pivot holes 700 are oval or oblong and serve to afford the trunnion tabs 342 with the ability to move axially back and forth and up and down in their corresponding pivot hole 700. As can be seen in FIG. 32, the trunnion tabs 342 may have a length "X" of, for example, approximately 0.060 inches and a height "Y" of, for example, approximately 0.050 inches. The pivot holes 700 have a proximal wall portion 702, a distal wall portion 704, an upper wall portion 706 and a lower wall portion 708. In various embodiments, for example, the distance "L" between the proximal wall 702 and the distal wall 704 may be approximately 0.120 inches and the distance "H" between the upper wall portion 706 and lower wall portion 708 may be approximately 0.090 inches. See FIG. 32. Those of ordinary skill in the art will appreciate that these distances and tolerances may, in connection with various embodiments, be somewhat dictated by the manufacturing tolerances attainable by the processes used to manufacture the anvil 340 and the elongate channel 302. In other embodiments, however, the distances "H", "L", "X", and "Y" may be sized relative to each other to enable the anvil 340 to travel along a closing path that is relatively substantially parallel to the top surface of a cartridge 500 supported in the elongate channel 302. Such arrangement serves to prevent or minimize the likelihood of tissue from being rolled out of between the anvil and the cartridge during clamping. Thus, these dimensions are merely exemplary and are not intended to be limiting. The trunnion tabs 342 and the pivot holes 700 may have other sizes, shapes and dimensions relative to each other that differ from such exemplary dimensions given herein that nevertheless enable those components to operate in the unique and novel manner of various embodiments of the present invention as described herein.

Figure 20:
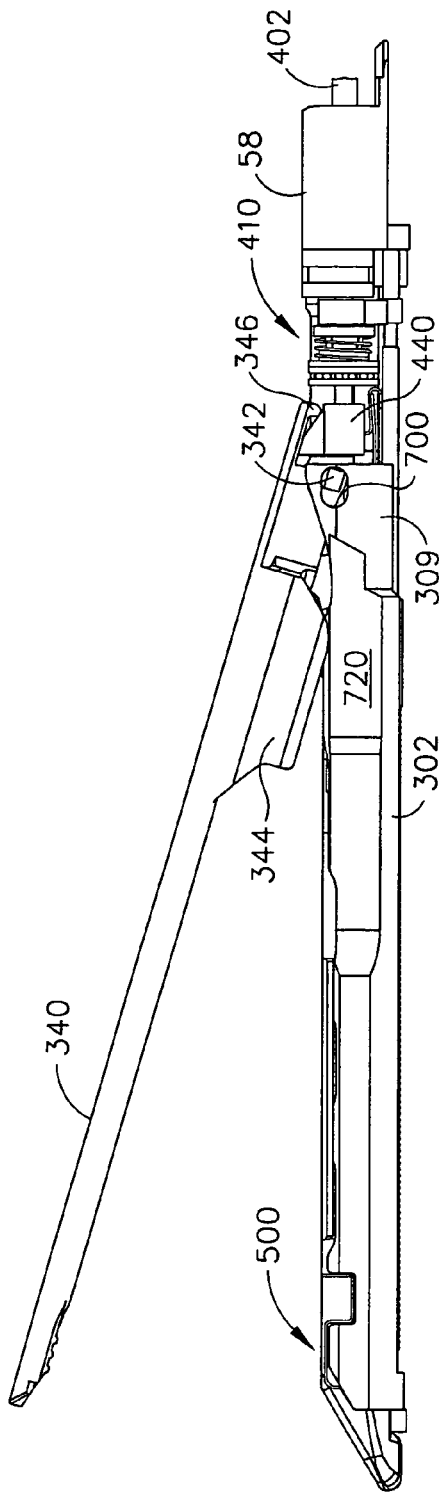
FIG. 20 is a side elevational view of various end effector embodiments of the present invention in an open position.
Figure 23:
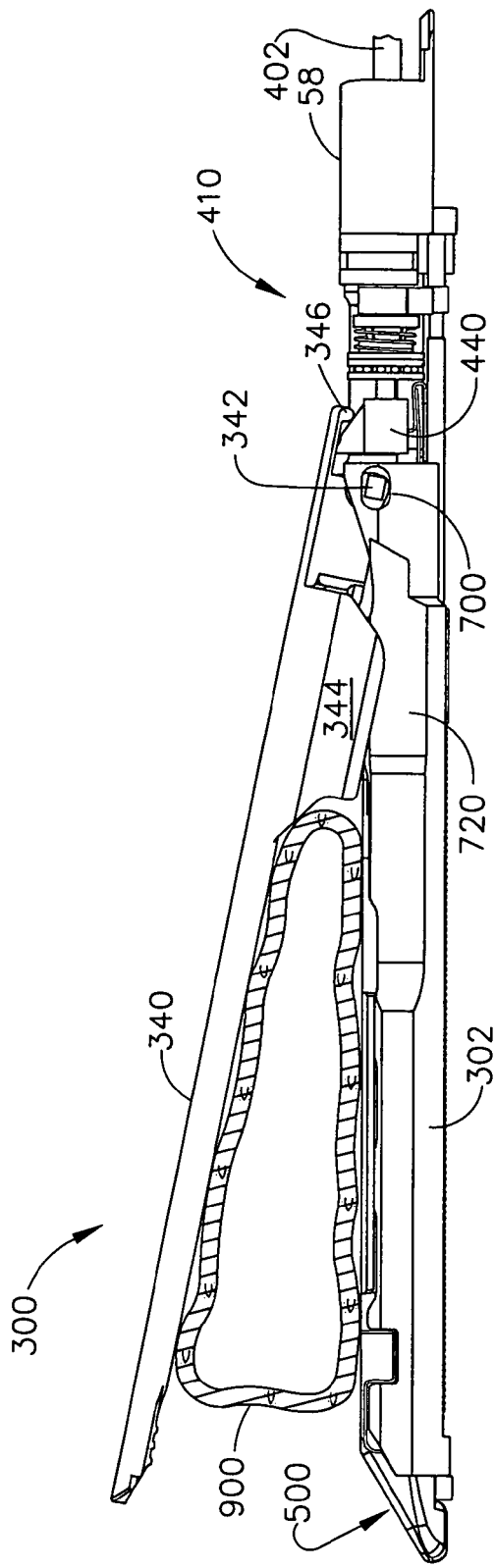
FIG. 23 is a side elevational view of an end effector of the present invention in an open position clamping a piece of tissue therein.
Figure 24:
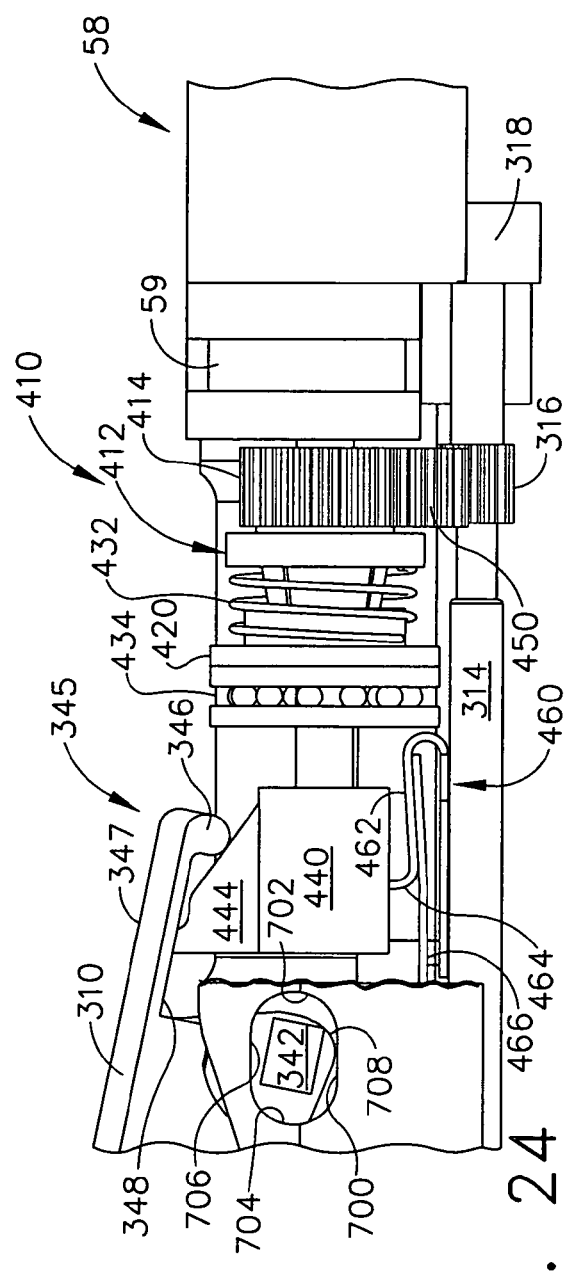
FIG. 24 is an enlarged partial cut away view of the end effector of FIG. 23.
Figure 25:
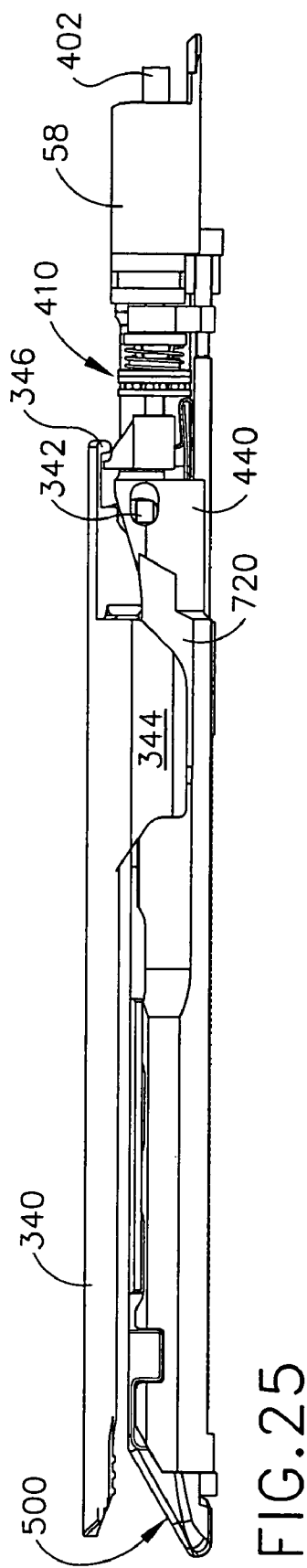
FIG. 25 is a side elevational view of various end effector embodiments of the present invention prior to being actuated to a closed position.
Figure 26:
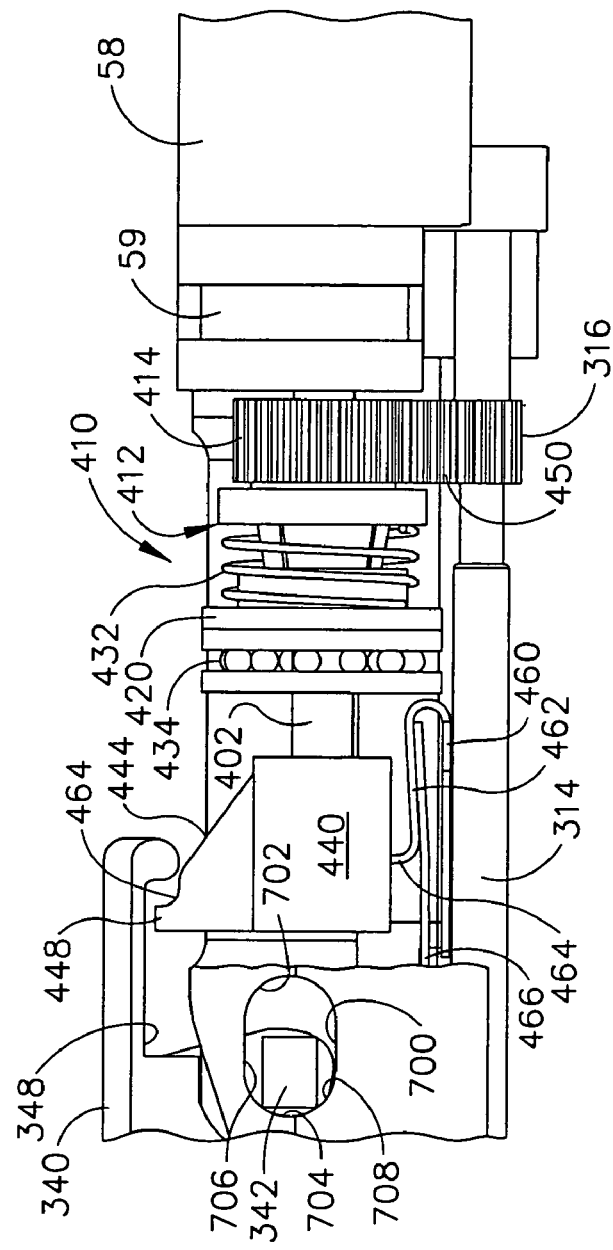
FIG. 26 is an enlarged partial cut away view of the end effector of FIG. 25.
Figure 29:
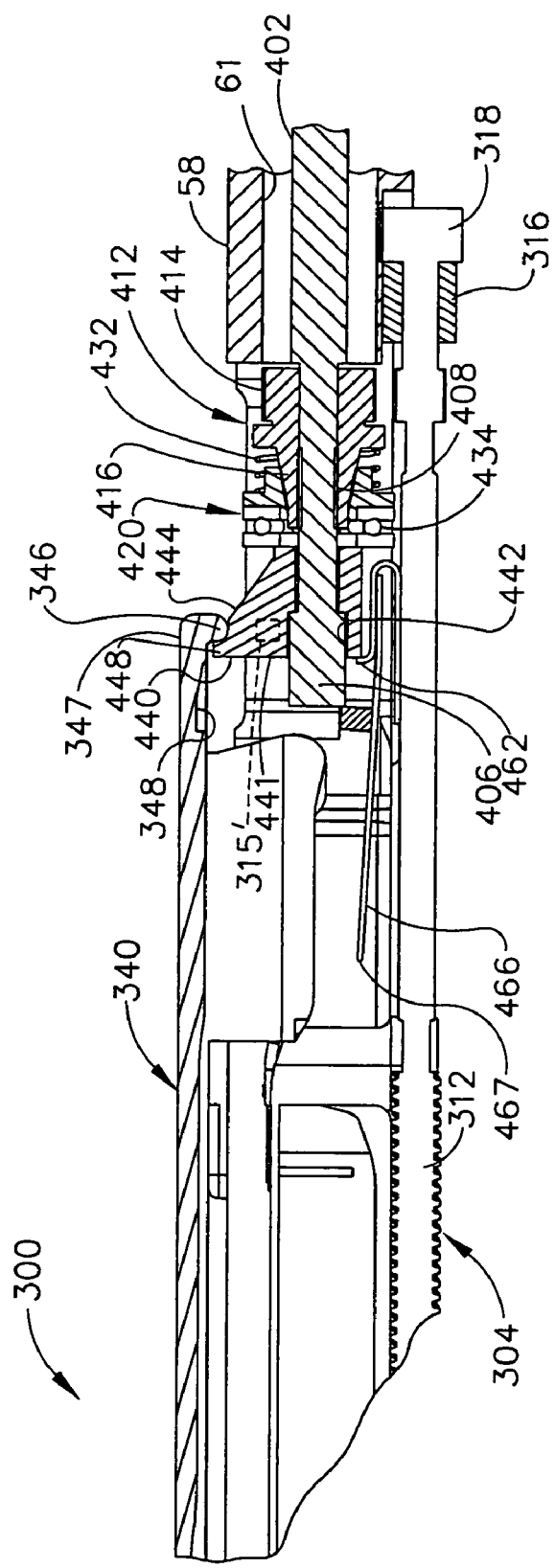
FIG. 29 is another enlarged partial cut away view of the end effector of FIGS. 27 and 28.

This ability of the trunnion tabs 342 to travel within their respective pivot hole 700 in the side walls of the 309 of the elongate channel 302 can be appreciated from reference to FIGS. 20-26. As can be seen in each of those Figures, the closure nut 440 is in its distal-most open position. When in that position, the retainer lip 464 of the closure lock spring is biased under the closure nut 440 and does not restrict the travel thereof. FIGS. 20 and 21 illustrate the trunnion tabs 342 adjacent the proximal end wall portions 702 of the pivot holes. FIGS. 23 and 24 illustrate the trunnion tabs 342 after they have crept somewhat midway between the proximal end wall portion 702 and the distal end wall portion 704 of the pivot hole 700. FIGS. 25 and 26 illustrate the trunnion tabs 342 after they have crept to a position adjacent the distal end wall portions 704 of the pivot holes 700. Thus, in various embodiments, the trunnion tabs 342 are loosely received within their respective pivot holes 700 and capable of moving axially, laterally and vertically or in combinations of such directions therein.

FIGS. 27-30 illustrate the anvil 340 in a closed position. As can be seen in FIG. 28, the trunnion tabs 342 are in abutting contact with a proximal end wall portion 702 of the pivot hole 700. When in that position (i.e., when the trunnion tabs 342 are held in abutting contact with proximal end wall portion 702), the staple-forming pockets 350 in the bottom surface 341 of the anvil 340 are in axial registration with corresponding staple-receiving pockets 512 in the cartridge 500 seated in the elongate channel 302 such that when the staples 534 are fired, they are correctly formed by the corresponding pockets 350 in the anvil 340. The anvil 340 is locked in that position by the retainer lip 464 portion of the closure lock spring 460 as will be discussed in further detail below.

Also in various embodiments, the anvil 340 is capable of moving laterally relative to the elongate channel due to manufacturing tolerances in the fabrication of the trunnion tabs 342 and the pivot holes 700. As can be seen in FIGS. 2-4, 20, 23, 27, and 31, in various embodiments, the anvil 340 is provided with a pair of downwardly extending tissue stops 344. During the clamping process, the tissue stops 344 essentially perform two functions. One of the functions consists of orienting the tissue 900 within the end effector 300 so as to prevent the tissue 900 from extending axially into the end effector 300 such that it extends beyond the innermost staple pockets 512 in the cartridge 500 when seated in the elongate channel 302. See FIG. 23. This prevents tissue 900 from being cut that is not stapled. The other function performed by the tissue stops 344 is to axially align the anvil 340 relative to the elongate channel 302 and ultimately to the cartridge 500 received therein. As the anvil 340 is closed, the tissue stops 344 serve to contact corresponding alignment surfaces 720 on the side of the elongate channel 302 and serve to laterally align the anvil 340 relative to the elongate channel 302 when the anvil 340 is closed and clamping tissue 900 such that the staple-forming pockets 350 in the bottom surface 341 of the anvil 340 are laterally aligned with the corresponding staple-receiving pockets 512 in the cartridge 500. See FIGS. 27 and 31.

The operation of various embodiments of the present invention will now be described with reference to FIGS. 20-29. FIGS. 20-26 illustrate the closure nut 440 in an open position. As can be seen in those Figures, when in the open position, the closure nut 440 is located such that the hook arm 346 is permitted to move to various positions relative thereto that enable the anvil 340 to pivot open to permit tissue 900 to be inserted between the anvil 340 and the elongated channel 302 and cartridge 500 seated therein. When in this position, the distal end 467 of the retainer arm 466 that is attached to the closure lock spring 460 is in contact with a ramp surface 321 formed on the proximal end of the knife assembly 320. See FIG. 22. As the knife assembly 320 moves proximally, the end of the retainer arm 466 contacts the ramp surface 321 on the proximal end of the knife assembly 320 and serves to cause the retainer arm 466 to bias the upper portion 462 of the closure lock spring 460 downward toward the bottom of the elongate channel 302. When the knife assembly 320 moves distally away from the retainer arm 466, the upper portion 462 of the closure lock spring 460 is permitted to spring upward to enable the retainer lip 464 to engage the closure nut 440 as will be further discussed below.

The reader will appreciate that when the end effector 300 is in the open positions depicted in FIGS. 20-26, the user can install a disposable cartridge assembly 500 in the elongate member 302. Also, when in those positions, the anvil 340 may be able to move axially, laterally and vertically relative to the elongate channel 302. In various embodiments, when the drive shaft 402 is rotated in a first direction, the closure thread 406 thereon threadably drives the closure nut 440 in the proximal direction (direction "B" in FIG. 8) until the closure threads 406 disengage the threaded hole 442 in the closure nut 440. See FIG. 13. As the closure nut 440 is driven proximally, the closure hook 346 on the anvil closure arm 347 rides up the ramp 444 of the closure nut 440 until it rides into the radiused portion 446 and contacts the closure tab 448. Such movement of the closure nut 440 serves to "pull" the anvil 340 to the closed position. See FIGS. 27-29. When in that position, the trunnion tabs 342 are in abutting contact with the proximal end portion 702 of the pivot holes 700 and the retainer lip 464 of the closure lock spring has engaged the distal end 441 of the closure nut 440 to retain the anvil 340 in the fully closed and axially aligned position. When also in that position, by virtue of the contact of the tissue stops 344 with the alignment surfaces 720 on the side walls 309 of the elongate channel 302, the anvil 340 is laterally aligned with the elongate channel 302 so that the staple forming pockets 350 in the anvil 340 are laterally aligned with corresponding the staple-receiving pockets 512 in the cartridge 500.

As the closure nut 440 is driven in the proximal direction, the proximal end 449 of the closure nut 440 contacts the thrust bearing 434 which forces the clutch plate 420 in the proximal direction against the force of clutch opening spring 432. Further travel of the closure nut 440 in the proximal direction drives the clutch plate 420 onto the tapered sections 416 of the tapered clutch member 412 which causes the male splines 418 therein to engage the female splines 408 on the distal drive shaft portion 402. Such engagement of the male splines 418 in the tapered clutch member 412 with the female splines on the distal drive shaft portion 402 causes the tapered clutch member 412 and the drive gear 414 to rotate with the distal drive shaft portion 402. Drive gear 414, in turn, rotates the knife screw gear 316 which causes the knife screw to rotate and drive the knife assembly distally ("A" direction).

As the knife assembly 320 is driven distally, it cuts the tissue and the cams 328 on the wedge sled 326 serve to drive the staple supporting drivers 532 upward which drive the staples 534 toward the anvil 340. As the legs 536 of the staples 534 are driven into the corresponding staple-forming pockets 350 in the anvil 340, they are folded over. See FIG. 7.

Figure 30:
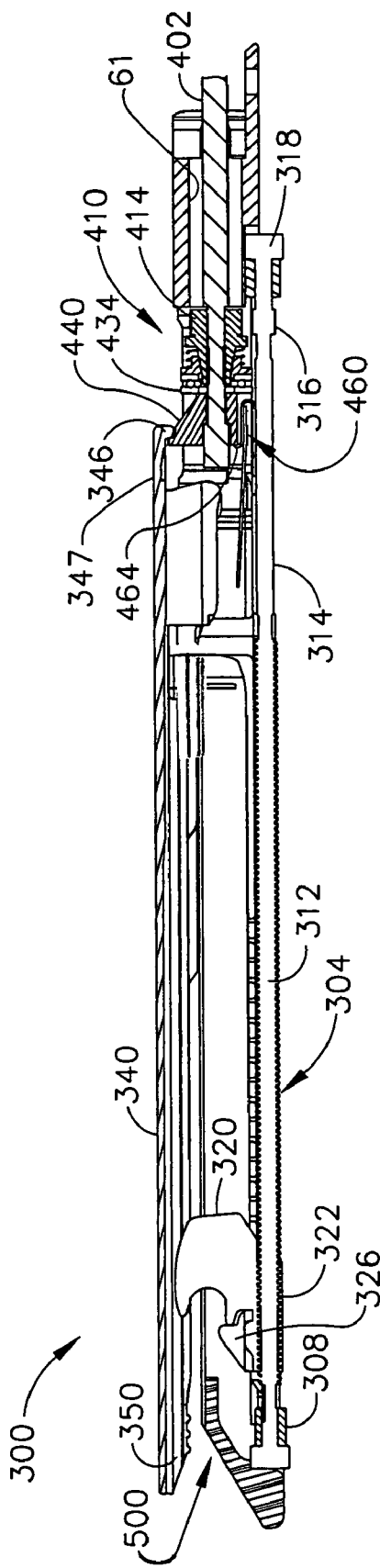
FIG. 30 is a cross-sectional view of the end effector of FIGS. 27-29 after the knife assembly has been driven to its distal-most position.

When the knife assembly 320 moves distally, the distal end 467 of the retainer arm 466 is no longer in contact with the ramp surface 321 of the knife assembly 320 which enables the retainer arm 466 and the upper portion 462 of the closure lock spring 460 to spring upwardly which further enables the retainer lip 464 on the closure lock spring 460 to retainingly engage the distal end 441 of the closure nut 440 to prevent it from moving distally. See FIGS. 28 and 29. By virtue of its contact with the closure nut 440 which is in contact with the thrust bearing 434, the retainer lip 464 serves to retain the clutch assembly 410 engaged with the distal drive shaft portion 402 until the knife assembly 320 once again returns to contact the distal end 467 of the retainer arm 464. After the knife assembly 320 has been driven to its final distal position as shown in FIG. 30, it activates a conventional sensor or contact 313 mounted within the elongate channel 302 and signals the control motor to stop driving the drive shaft 402. See FIG. 4. Those of ordinary skill in the art will understand that a variety of different control arrangements could be employed to control the drive shaft 402. For example, when the knife assembly 310 reaches its distal-most position and activates the sensor 313, the control system 610 housed within the handle 6 could automatically reverse the drive motor 600 therein and cause the drive shaft portion 402 and knife screw to reverse direction (e.g., move in the proximal "B" direction). In various other embodiments, the control system 610 may simply stop the drive motor 600 and then require the surgeon to activate a button 30 to cause the motor 600 to reverse. In still other arrangements, the control system 610 may institute a predetermined timed delay between the time that the reversing sensor 313 is activated and the time that the motor 600 is reversed.

As the knife assembly 320 moves in the proximal direction on the knife screw 304, the closure threads 406 on the drive shaft 402 begin to screw back into the threaded hole portion 442 in the closure nut 440. During this process, the ramp surface 321 of the knife assembly 320 again contacts the distal end 467 of the retainer arm 466 which serves to bias the upper portion 462 of the closure lock spring 460 toward the bottom of the elongate channel 302 to permit the retainer lip 464 to disengage from the distal end 441 of the closure nut 440 thereby permitting the clutch opening spring 432 to bias the clutch assembly 410 and closure nut 440 distally. As the closure nut 440 moves distally, the closure hook 346 on the anvil 340 rides up the ramp 444 on the closure nut 440 until the closure nut 440 reaches the open position wherein the closure tab 448 is received within the tab relief groove 348 in the bottom surface 341 of the anvil 340 and the closure nut 440 moves the anvil assembly 372 to the open position. A second conventional sensor or contact 315 is mounted within the proximal end portion 305 of the elongate channel 302 for sensing when the closure nut 440 is in the open position and communicates with the motor to cause it to stop. See FIG. 4.

As indicated above, a variety of different motor/control arrangements may be employed to power the drive shaft portion 402. For example, in various embodiments when the closure trigger 18 is actuated, that is, drawn in by a user of the instrument 10, the motor 600 may commence the above described closing process. A third sensor 315' may be used in the elongate channel member 302 to sense when the closure nut 404 has moved into the closed position (shown in FIG. 28). When the third sensor 315' senses that the closure nut 440 is in that position, the sensor 315' may cause the motor 600 to stop rotating. Thereafter, if the surgeon is satisfied with the clamping of the tissue in the end effector 300, the surgeon may actuate the firing trigger 20 or other actuator arrangement to activate the motor 600 to rotate the drive shaft 402 which drives the knife screw 304 in the above-mentioned manner.

Figure 33:
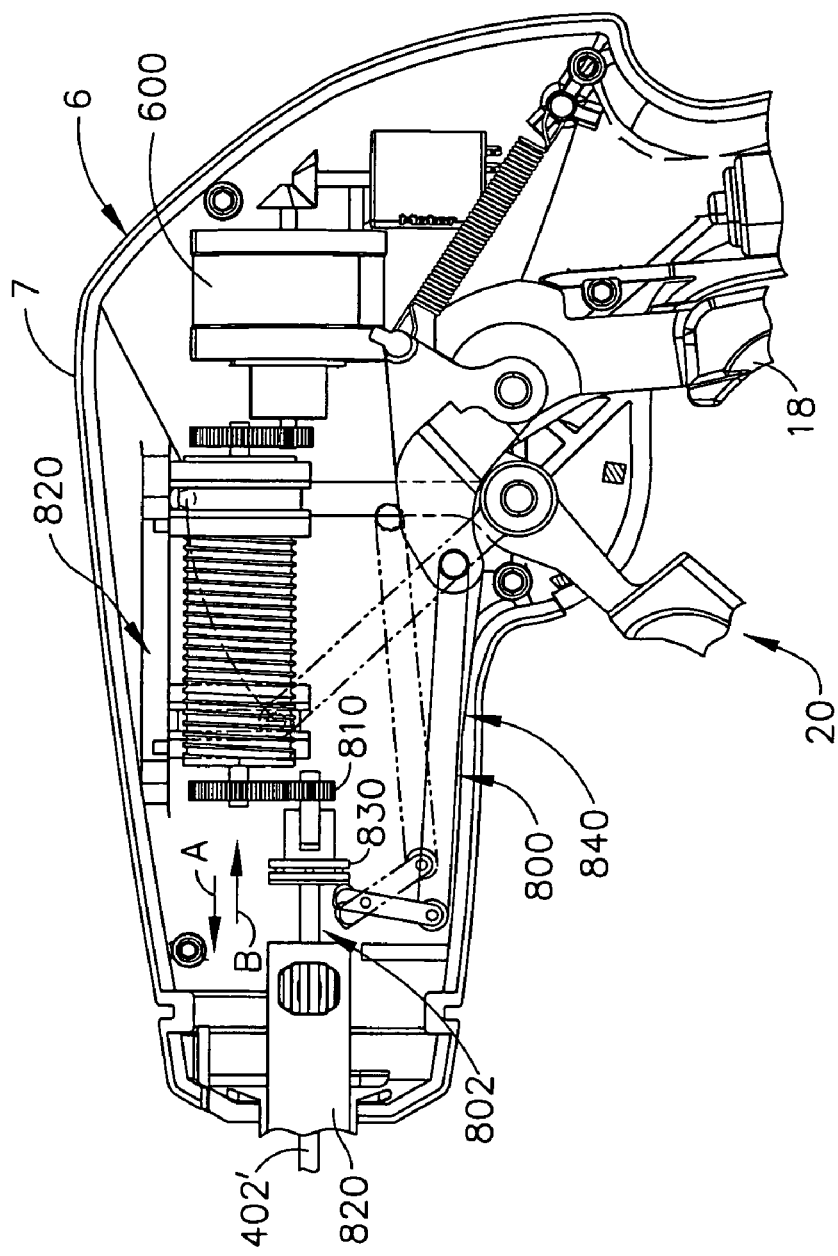
FIG. 33 is a cross-sectional view of a control handle of various embodiments of the present invention.
Figure 34:
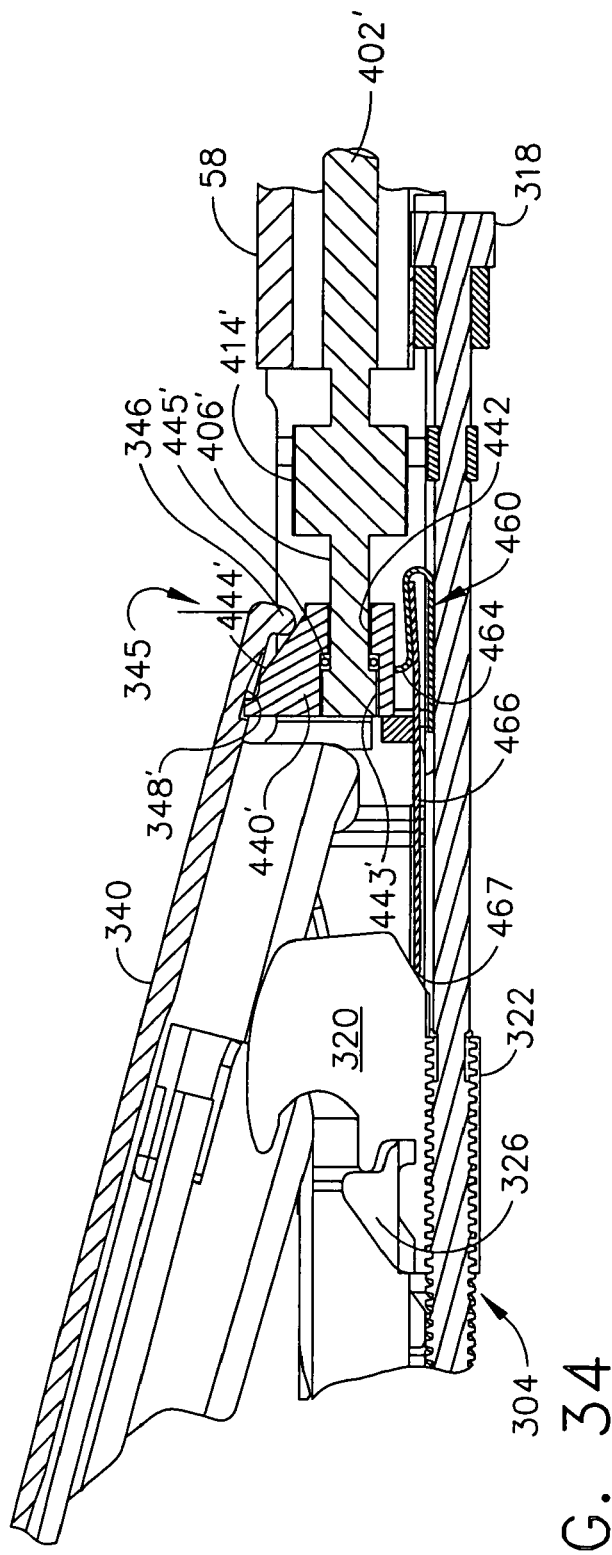
FIG. 34 is a partial cross-sectional view of a portion of another end effector embodiment of the present invention in an open position.
Figure 35:
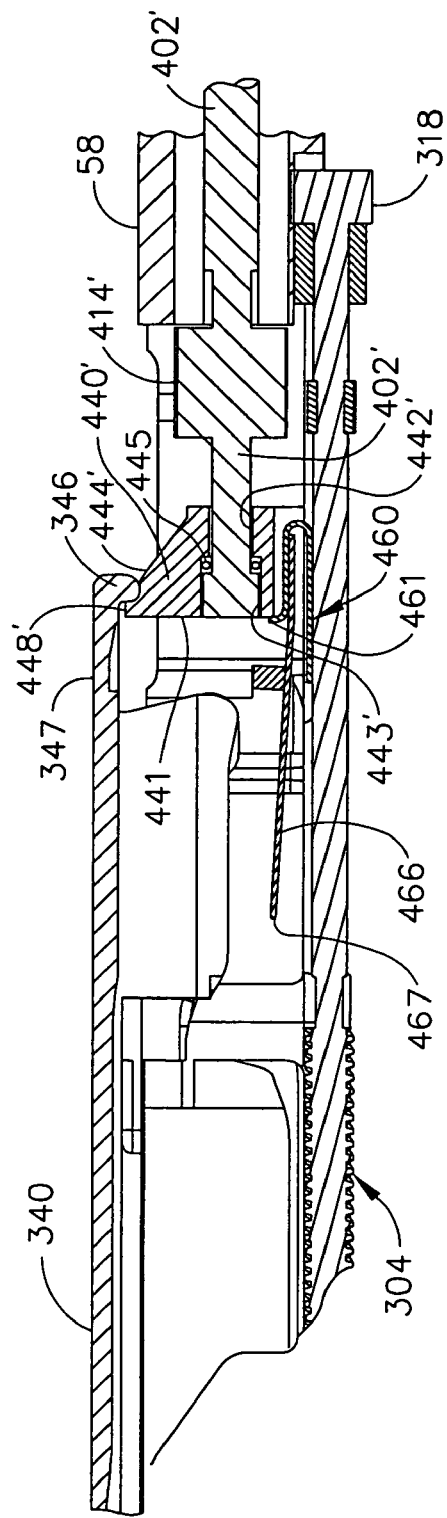
FIG. 35 is a partial cross-sectional view of the end effector of FIG. 34 in a closed position.

Another drive arrangement is depicted in FIGS. 33-35. In this embodiment, a closure wedge 440' is axially moved by a manual drive assembly 800. More specifically and with reference to FIG. 33, the proximal end 802 of the drive shaft 402' is has a drive gear 810 attached thereto. Although a variety of different gear and motor arrangements may be employed, the drive gear 810 may be oriented for selective meshing engagement with a gear train or transmission assembly generally designated as 820 that is ultimately driven my motor 600. The drive shaft 402' is movably supported by a proximal spine tube segment 820 that is pivotally coupled to the distal spine tube segment 58 as described in various of the U.S. patent applications incorporated by reference herein above and rigidly attached to the housing portions 7 of the handle 6. In other arrangements wherein the end-effector is not capable of articulating travel, the distal spine tube 58 may be longer and rigidly coupled to the sections 7 of the handle 6. Regardless of which spine tube arrangement is employed, the drive shaft 402' is axially and rotatably received therein such that the drive shaft 402' can move axially in the distal and proximal directions and also rotate when engaged with the motor 600.

Various methods may be employed to mechanically move the drive shaft 402' in the distal and proximal directions. For example, as shown in FIG. 33, a thrust bearing assembly 830 may be attached to the drive shaft 402' for selective contact by a control linkage assembly 840. As can be seen in that Figure, the control linkage assembly 840 may be linked to the closure trigger 18 and capable of biasing the drive shaft 402' in the proximal ("B") direction when the closure 18 is pivoted in the proximal direction, the control linkage assembly contacts the thrust bearing and pulls the drive shaft 402 in the proximal direction.

Turning next to FIGS. 34 and 35, as can be seen in these Figures, the distal end 406' of the drive shaft is rotatably supported within a closure wedge 440' that is similar in construction as closure nut 440 as described above. In particular, the closure wedge 440' has a proximal hole 442' and a distal hole portion 443' that is larger in diameter than the proximal hole portion 442'. The distal end 406' of the drive shaft 402' is rotatably supported in the distal hole portion 443' by a bearing 445'. The distal end portion 406' of the drive shaft 406' is longer than the hole 403' such that as the drive shaft 402' moves distally and proximally, it cannot become disengaged from the wedge 440'. The wedge 440' also has a closure ramp portion 444', a radiused portion 446', and a closure tab 448' formed thereon. As can be seen in FIGS. 34 and 35, a drive gear 414' is attached to the drive shaft 402' and is adapted to mesh with the transfer gear 450 that is in meshing engagement with the knife screw gear 316.

In these embodiments, when the user wishes to close the anvil 340, the user moves the closure trigger 18 toward the handle 6. This action causes the control linkage assembly 840 to move the drive shaft 402' in the proximal direction and pull the wedge 440' proximally. As the wedge 440' moves proximally, the closure hook 346 on the proximal end 345 of the anvil 340 rides up the ramp portion 444' thereon until the it is seated in the radiused portion 446' of the wedge 440'. The wedge 440' gets biased proximally until the retainer lip 464 engages the distal end 441' of the wedge 440' as shown in FIG. 35. When in that position, the trunnion tabs 342 of the anvil 340 are in engagement with the proximal end portion 702 of pivot holes 700 as described above. Also when in that position, the drive gear 414' is now in meshing engagement with the transfer gear 450 (not shown in FIG. 35) that is in meshing engagement with the knife screw gear 316. Thus, when the drive shaft 402' is rotated by activating the control motor, the drive gear 414' serves to drive the transfer gear 450 and the knife screw gear 316 to drive the knife assembly 320 in the above described manner. The closure lock spring 460 and the motor control sensors in the elongate channel operate in the above described manner.

After the drive motor 600 has reversed the rotation of the drive shaft 402' which drives the knife assembly 320 proximally back to its starting position wherein the ramp surface 321 contacts the distal end 467 of the retainer arm 466, the lip 464 of the closure lock spring 460 is biased downwardly to permit the wedge 440' to move distally. The user can then release the closure trigger 18 which is spring biased to the unactuated position shown in FIG. 1. As the closure trigger 18 returns to the unactuated position, the control linkage assembly 840 permits the drive shaft 402' and wedge 440' to move distally and open the anvil 340 in the above-described manner.

The reader will understand that various embodiments of the present invention provide vast improvements over prior end effectors and end effector drive arrangements. In particular, the various unique and novel drive system of various embodiments of the present invention permit the anvil and elongated channel components of the end effector to be manufactured utilizing materials and processes that are more economical than other materials and processes used in the past without sacrificing performance. In addition, by providing an anvil that can travel along a closing path that is substantially parallel to the elongate channel and staple cartridge housed therein, reduces the likelihood that the tissue will be rolled out of position during the initial closing of the anvil.

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical cuffing and fastening instrument comprising:
   a control handle;
   an elongate channel coupled to said control handle and sized to support a cartridge therein, said elongate channel defining a longitudinal axis;
   an anvil having a pair of trunnions protruding therefrom, each said trunnion received in a corresponding elongate pivot hole formed in said elongate channel to pivotally couple said anvil to said elongate channel, said trunnions defining a pivot axis that is substantially transverse to said longitudinal axis, said elongate pivot holes sized relative to said trunnions to facilitate axial travel of said pivot axis within said elongate pivot holes and such that said anvil is selectively pivotable between open and closed positions relative to said elongate channel;
   a drive system operably supported in said elongate channel; and
   a closure nut movably supported in said channel and responsive to separate opening and closing motions from said drive system, said closure nut configured to coact with said anvil such that upon receiving a closing motion from said drive system, said closure nut pulls the entire said anvil relative to said elongate channel to cause said anvil to close and axially move to an aligned position relative to said elongate channel and upon application of an opening motion to said closure nut, said closure nut causes said anvil to move to an open position relative to said elongate channel.

2. The surgical cutting and fastening instrument of claim 1 wherein as said anvil is pulled to said closed position, a bottom surface of said anvil is maintained in a substantially parallel position relative to a top surface of a cartridge seated in said elongate channel.

3. The surgical cuffing and fastening instrument of claim 1 wherein said closure nut is threaded onto a rotary drive member that is operably supported in said elongate channel, said rotary drive member controlled by a control system in said control handle.

4. The surgical cuffing and fastening instrument of claim 1 further comprising tissue stops on said anvil, said tissue stops coacting with said elongate channel to laterally align said anvil thereon as said anvil is moved to said closed position.

5. The surgical cuffing and fastening instrument of claim 1 further comprising a knife assembly operably supported within said elongate channel and coupled to said drive system for receiving control motions therefrom.

6. The surgical cuffing and fastening instrument of claim 5 wherein said knife assembly is threaded on a knife screw that is rotatably supported within said elongate channel and coupled to said drive system for receiving rotary driving motions therefrom.

7. The surgical cuffing and fastening instrument of claim 6 wherein said drive system comprises:
   a drive shaft configured to receive rotary motion from a motor in said control handle;
   a gear assembly coupled to said drive shaft and knife screw to transmit rotary motion from said drive shaft to said knife screw.

8. The surgical cuffing and fastening instrument of claim 7 wherein said gear assembly comprises:
   a drive gear engagably and disengagably journaled on said drive shaft; and
   a transfer gear in meshing engagement with said drive gear and a knife screw gear on said knife screw.

9. The surgical cuffing and fastening instrument of claim 8 wherein said closure nut is threadably receiving on a closure thread formed on said drive shaft such that upon rotation of said drive shaft in a first direction, said closure nut moves in a proximal direction to pull said anvil to said closed position and upon rotation of said drive shaft in a second direction, said closure threaded moves in a distal direction to open said anvil.

10. The surgical cuffing and fastening instrument of claim 9 further comprising a clutch assembly movably received on said drive shaft and having said drive gear attached thereto, said clutch assembly selectively engagable with said drive shaft for rotatable travel therewith upon contact by said closure nut when said closure nut is moved proximally to close said anvil and to rotatably disengage said drive shaft upon when said closure nut has moved distally to cause said anvil to open.

11. The surgical cuffing and fastening instrument of claim 10 wherein said clutch assembly comprises:
   a tapered clutch member movably received on said drive shaft, said tapered clutch member having a series of male splines therein oriented to engage and disengage a series of female splines on said drive shaft, said tapered clutch member supporting said drive gear thereon;
   a clutch plate received on said tapered clutch member and being movable between an engaged position wherein said clutch plate urges said male splines of said tapered clutch member into meshing engagement with said female splines on said drive shaft and a disengaged position wherein said male splines on said tapered clutch member are not engaged with said female splines on said drive shaft;
   a spring between said tapered clutch member and said clutch plate to bias said clutch plate to said disengaged position; and
   a thrust bearing on said drive shaft between said clutch plate and said closure nut.

12. The surgical cuffing and fastening instrument of claim 1 wherein each of said elongate pivot holes have a proximal end portion and a distal end portion opposite to said distal end portion, said trunnion tabs contacting said proximal end portions of said corresponding elongate pivot holes to axially align said anvil on said elongate channel.

13. The surgical cuffing and fastening instrument of claim 1 wherein said oversized pivot holes are oval-shaped.

14. A surgical cutting and fastening instrument comprising:
   a control handle;
   an elongate channel coupled to said control handle and sized to support a cartridge therein;
   an anvil having a pair of trunnions protruding therefrom, each said trunnion received in a corresponding elongate pivot hole formed in said elongate channel to pivotally couple said anvil to said elongate channel, said trunnions defining a pivot axis about which said anvil may selectively pivot relative to said elongate channel between open and closed positions, said elongate pivot holes sized relative to said trunnions to facilitate axial travel of said pivot axis within said elongate pivot holes; and
   a closure wedge supported on a drive member that operably extends into a portion of said elongate channel and being configured to coact with said anvil, said drive member controlled by a control system in said control handle and being axially movable relative to said elongate channel such that upon application of a closing motion to said drive member, said drive member causes said closure wedge to pull the entire- said anvil relative to said elongate channel to cause said anvil to move to a closed position wherein said anvil is aligned relative to said elongate channel and upon application of an opening motion to said drive member said closure wedge causes said anvil to move to an open position relative to said elongate channel.

15. The surgical cutting and fastening instrument of claim 14 wherein said drive member axially moves in a proximal direction upon application of said closing motion thereto and wherein said drive member axially moves in a distal direction upon application of said opening motion thereto.

16. The surgical cutting and fastening instrument of claim 15 further comprising a knife assembly operably supported within said elongate channel and coupled to drive member such that upon application of a first rotary motion to said drive member by said control system, said drive member causes said knife assembly to be driven in said distal direction within said elongate channel and upon application of a second rotary motion to said drive member by said control system, said drive member causes said knife assembly to be driven proximally in said elongate channel.

17. The surgical cutting and fastening instrument of claim 16 wherein said knife assembly is movably supported on an elongated knife screw rotatably supported within said elongate channel and wherein said drive member further comprises a drive gear on said drive member oriented to transmit rotation to said knife screw upon application of said closure force to said drive member to cause said drive member to axially move to a closed position.

18. The surgical cutting and fastening instrument of claim 17 further comprising:
   a knife screw gear on said knife screw; and
   a transfer gear in meshing engagement with said knife screw gear and oriented for selective meshing engagement with said drive gear when said drive member has moved to said closed position.

19. The surgical cutting and fastening instrument of claim 14 further comprising a closure actuator on said control handle and operably coupled to said drive member such that upon movement of said closure actuator to a closed position, said drive member is moved in a proximal direction to apply a pulling force to said closure wedge and upon movement of said closure actuator to an open position, said drive member is moved in a distal direction to cause said closure wedge to open said anvil.

20. A surgical cuffing and fastening instrument comprising:
   control means;
   means for supporting a cartridge, said means for supporting attached to said control means;
   an anvil having a pair of trunnions protruding therefrom, each said trunnion received in a corresponding elongate pivot hole formed in said means for supporting to pivotally couple said anvil to said means for supporting, said trunnions defining a pivot axis that is substantially transverse to said longitudinal axis, said elongate pivot holes sized relative to said trunnions to facilitate axial travel of said pivot axis within said elongate pivot holes such that the entire said anvil is axially and laterally movable relative to said means for supporting and selectively pivotable between open and closed positions relative to said means for supporting; and
   drive means supported in said means for supporting, said drive means selectively pulling the entire said anvil relative to said elongate channel to cause said anvil to close and move to an aligned position relative to said means for supporting and selectively applying an opening force to said anvil to cause said anvil to move to an open position relative to said means for supporting.

21. A surgical cuffing and fastening instrument comprising:
   a control handle;

an elongate channel coupled to said control handle and sized to support a cartridge therein, said elongate channel having a pair of oversized pivot holes defined therein;

an anvil pivotally coupled to said elongate channel within said oversized pivot holes such that the entire said anvil is axially and laterally movable relative to said elongate channel and selectively pivotable between open and closed positions relative to said elongate channel;

a drive shaft configured to receive rotary motion from a motor in said control handle;

a drive gear engagably and disengagably journaled on said drive shaft;

a knife assembly threaded on a knife screw that is rotatably supported within said elongate channel;

a transfer gear in meshing engagement with said drive gear and a knife screw gear on said knife screw; and a closure nut movably supported in said channel and responsive to separate opening and closing motions from said drive system, said closure nut configured to coact with said anvil such that upon receiving a closing motion from said drive system, said closure nut pulls the entire said anvil relative to said elongate channel to cause said anvil to close and axially move to an aligned position relative to said elongate channel and upon application of an opening motion to said closure nut, said closure nut causes said anvil to move to an open position relative to said elongate channel.

22. The surgical cuffing and fastening instrument of claim 21 wherein said closure nut is threadably receiving on a closure thread formed on said drive shaft such that upon rotation of said drive shaft in a first direction, said closure nut moves in a proximal direction to pull said anvil to said closed position and upon rotation of said drive shaft in a second direction, said closure threaded moves in a distal direction to open said anvil.

23. The surgical cuffing and fastening instrument of claim 22 further comprising a clutch assembly movably received on said drive shaft and having said drive gear attached thereto, said clutch assembly selectively engagable with said drive shaft for rotatable travel therewith upon contact by said closure nut when said closure nut is moved proximally to close said anvil and to rotatably disengage said drive shaft upon when said closure nut has moved distally to cause said anvil to open.

24. The surgical cuffing and fastening instrument of claim 23 wherein said clutch assembly comprises:
a tapered clutch member movably received on said drive shaft, said tapered clutch member having a series of male splines therein oriented to engage and disengage a series of female splines on said drive shaft, said tapered clutch member supporting said drive gear thereon;
a clutch plate received on said tapered clutch member and being movable between an engaged position wherein said clutch plate urges said male splines of said tapered clutch member into meshing engagement with said female splines on said drive shaft and a disengaged position wherein said male splines on said tapered clutch member are not engaged with said female splines on said drive shaft;
a spring between said tapered clutch member and said clutch plate to bias said clutch plate to said disengaged position; and
a thrust bearing on said drive shaft between said clutch plate and said closure nut.

25. A surgical cuffing and fastening instrument comprising:
a control handle;
an elongate channel coupled to said control handle and sized to support a cartridge therein, said elongate channel having a pair of oversized pivot holes defined therein;
an anvil pivotally coupled to said elongate channel within said oversized pivot holes such that said anvil is axially and laterally movable relative to said elongate channel and selectively pivotable between open and closed positions relative to said elongate channel; and
a closure wedge supported on a drive member that operably extends into a portion of said elongate channel and being configured to coact with said anvil, said drive member controlled by a control system in said control handle and being axially movable relative to said elongate channel such that upon application of a closing motion to said drive member, said drive member axially moves in a proximal direction to cause said closure wedge to apply a pulling force to said anvil to cause said anvil to move to a closed position wherein said anvil is aligned relative to said elongate channel and, upon application of an opening motion to said drive member, said closure wedge causes said anvil to move to an open position relative to said elongate channel;
a knife assembly movably supported on an elongated knife screw rotatably supported within said elongate channel;
a drive gear on said drive member oriented to transmit rotation to said knife screw upon application of said closure force to said drive member to cause said drive member to axially move to a closed position,
a knife screw gear on said knife screw; and
a transfer gear in meshing engagement with said knife screw gear and oriented for selective meshing engagement with said drive gear when said drive member has moved to said closed position.

26. A surgical cutting and fastening instrument comprising:
a control handle;
an elongate channel coupled to said control handle and sized to support a cartridge therein, said elongate channel defining a longitudinal axis;
an anvil having a pair of trunnions protruding therefrom, each said trunnion received in a corresponding elongate pivot hole formed in said elongate channel to pivotally couple said anvil to said elongate channel, said trunnions defining a pivot axis that is substantially transverse to said longitudinal axis, said elongate pivot holes sized relative to said trunnions to facilitate axial travel of said pivot axis within said elongate pivot holes and said anvil is selectively pivotable between open and closed positions relative to said elongate channel; and
a drive system operably supported in said elongate channel and configured to selectively apply separate opening and closing motions to said anvil such that, upon receiving a closing motion from said drive system, said anvil is caused to close and axially move to an aligned position relative to said elongate channel and upon application of said opening motion to anvil, said anvil is caused to move to an open position relative to said elongate channel.

27. A surgical cutting and fastening instrument comprising:
a control handle;
an elongate channel coupled to said control handle and sized to support a cartridge therein, said elongate channel having a pair of oversized pivot holes defined therein;

an anvil pivotally coupled to said elongate channel by a pair of trunnion tabs formed on a proximal end of said anvil and received within corresponding said oversized pivot holes in said elongate channel such that said trunnion tabs are axially and laterally movable therein and said anvil is axially and laterally movable relative to said elongate channel and selectively pivotable between open and closed positions relative to said elongate channel;

a drive system operably supported in said elongate channel; and a closure nut movably supported in said channel and responsive to separate opening and closing motions from said drive system, said closure nut configured to coact with said anvil such that upon receiving a closing motion from said drive system, said closure nut pulls said anvil to cause said anvil to close and axially move to an aligned position relative to said elongate channel and upon application of an opening motion to said closure nut, said closure nut causes said anvil to move to an open position relative to said elongate channel.

* * * * *

UNITED STATES PATENT AND TRADEMARK OFFICE
CERTIFICATE OF CORRECTION

PATENT NO. : 7,464,849 B2  
APPLICATION NO. : 11/344021  
DATED : December 16, 2008  
INVENTOR(S) : Frederick E. Shelton, IV, Stephen J. Balek and Eugene L. Timperman Page 1 of 1

It is certified that error appears in the above-identified patent and that said Letters Patent is hereby corrected as shown below:

Col. 13 Line 63, Col. 14 Lines 31, 34, 38, 42, 47, 54 and 60, Col. 15 Lines 1, 10, 30 and 36, Col. 16 Lines 40 and 65, Col. 17 Line 29, 37, 46 and 66.

Error in

Claims 1, 3-13 and 20-25 recite a "surgical <u>cuffing</u> and fastening instrument"

Correct to

Claims 1, 3-13 and 20-25 recite a "surgical cutting and fastening instrument."

Signed and Sealed this  
Sixth Day of March, 2012

David J. Kappos  
*Director of the United States Patent and Trademark Office*